（12）United States Patent
Tanabe et al.

(10) Patent No.: US 8,460,577 B2
(45) Date of Patent: Jun. 11, 2013

(54) POLYMERIZABLE OXETANE DERIVATIVE

(75) Inventors: Mayumi Tanabe, Chiba (JP); Yoshiharu Hirai, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

(21) Appl. No.: 12/947,192

(22) Filed: Nov. 16, 2010

(65) Prior Publication Data

US 2011/0114882 A1    May 19, 2011

(30) Foreign Application Priority Data

Nov. 18, 2009   (JP) .................................. 2009-262663
Oct. 6, 2010    (JP) .................................. 2010-226477

(51) Int. Cl.
| *C09K 19/00* | (2006.01) |
| *C09K 19/06* | (2006.01) |
| *C09K 19/32* | (2006.01) |
| *C09K 19/52* | (2006.01) |
| *G02F 1/1333* | (2006.01) |

(52) U.S. Cl.
USPC .............. 252/299.61; 252/299.01; 252/299.6; 252/299.62; 252/299.63; 252/299.64; 252/299.65; 252/299.66; 252/299.67; 560/8; 549/510; 428/1.1; 428/1.3

(58) Field of Classification Search
USPC .... 549/510; 560/8; 428/1.1, 1.3; 252/299.01, 252/299.6, 299.61, 299.62, 299.63, 299.64, 252/299.65, 299.66, 299.67
See application file for complete search history.

(56) References Cited

U.S. PATENT DOCUMENTS

| 7,682,522 | B2 * | 3/2010 | Tanabe ...................... 252/299.63 |
| 7,794,802 | B2 * | 9/2010 | Itoh ................................ 428/1.1 |
| 2009/0121187 | A1 | 5/2009 | Tanabe |
| 2010/0103366 | A1 * | 4/2010 | Farrand et al. ................ 349/183 |

FOREIGN PATENT DOCUMENTS

JP      08-020641    1/1996

OTHER PUBLICATIONS

Lee et al., "Ferroelectric liquid crystalline polyoxetanes bearing chiral dimesogenic pendants", Journal of Materials chemistry, 2002, 12, 2225-2230.

* cited by examiner

*Primary Examiner* — Geraldina Visconti
(74) *Attorney, Agent, or Firm* — J.C. Patents

(57) ABSTRACT

The invention provides a compound represented by formula (1).

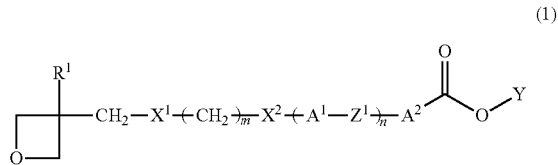

In the formula (1), $R^1$ is hydrogen, methyl or ethyl; $X^1$ is a single bond, —O— or —OCO—; $X^2$ is a single bond, —O—, —COO— or —OCO—; $A^1$ and $A^2$ are each independently a divalent aromatic ring or a divalent cyclohexane ring, and in these rings, arbitrary hydrogen may be replaced by halogen, alkyl having 1 to 3 carbons or halogenated alkyl having 1 to 3 carbons; $Z^1$ is independently a single bond, —O—, —S—, —COO—, —OCO—, —CH$_2$O—, —OCH$_2$—, —CH=CH—COO—, —OCO—CH=CH—, —CH$_2$CH$_2$—COO—, —OCO—CH$_2$CH$_2$—, —CON(R)— or —N(R)CO—; R is hydrogen or methyl; Y is a terpenoid residue or a steroid residue; m is an integer from 0 to 20; and n is an integer from 0 to 3.

11 Claims, No Drawings

POLYMERIZABLE OXETANE DERIVATIVE

CROSS-REFERENCE TO RELATED APPLICATION

This application claims the priority benefit of Japan application serial no. 2009-262663, filed on Nov. 18, 2009 and Japan application serial no. 2010-226477, filed on Oct. 6, 2010. The entirety of each of the above-mentioned patent applications is hereby incorporated by reference herein and made a part of specification.

BACKGROUND OF THE INVENTION

1. Field of the Invention

The present invention relates to a new oxetane derivative. It relates more particularly to a polymerizable oxetane derivative, which is an optically active compound that can be used as a chiral agent, and also relates to a liquid crystal composition including the oxetane derivative, a polymer obtained from the composition, and their use.

2. Related Art

Cholesteric liquid crystal molecules have a helical structure in their liquid crystal state. Because of this, they reflect circularly polarized light with a specific wavelength range, depending on the rotating direction and the pitch length of the helix of the liquid crystal molecules, when the helical structure fixed by the polymerization of the cholesteric liquid crystal molecules is irradiated with light. For example, light with wavelengths of blue, green, yellow and red, which correspond to the pitch length of liquid crystals, is selectively reflected on irradiation with visible light. These color tones are different from those of pigment or dye, in which colors arise from light absorption, and have viewing angle-dependence in which a color tone varies on the basis of viewing angles. Moreover, since the pitch length of the cholesteric liquid crystals can be adjusted according to the temperature and the kind of the liquid crystals, not only visible light but also light in the infrared and ultraviolet ranges can be selectively reflected.

Materials that selectively reflect light with various wavelengths in a wide wavelength range have been used by utilizing such characteristics of the cholesteric liquid crystals. The materials are included in liquid crystal pigments, coating materials, spray inks, printing inks, cosmetics, anti-counterfeit printed matters, ornaments, and the like. Use of the materials for an optical film such as a polarizing plate, a compensation plate and a color filter in an optical device such as a liquid crystal display device and a holographic device has been proposed. With respect to the existing liquid crystal pigment, a flaked cholesteric liquid crystal polymer and microcapsulated cholesteric liquid crystals have been used. These usages are for automobile coatings, cosmetics and so forth.

Cholesteric liquid crystals can usually be prepared by the addition of an optically active compound (a chiral agent) to nematic liquid crystals. The cholesteric liquid crystals require a helical structure with a quite short helical pitch in order to reflect circularly polarized light in the range of ultraviolet light to visible light. In this case, the optically active compound is required to have a large helical twist power (a HTP). When an optically active compound with a small HTP is used, the amount of the compound should be increased. However, an increase of the amount causes disappearance of liquid crystallinity of the mixture with cholesteric liquid crystals and an objective cholesteric phase cannot be obtained, since an ordinary optically active compound has no liquid crystallinity. Thus, it is difficult to adjust characteristics, especially the temperature range of a cholesteric phase or a wavelength range that allow selective reflection, when the HTP of the optically active compound is small.

When an optical film is produced, a polymerizable chiral agent is added to a polymerizable liquid crystal compound, and a polymer is formed, fixing a helical structure. Such a chiral agent is required to have characteristics such as a large HTP, a small temperature dependence of the HTP, an excellent compatibility with the liquid crystal compound and an excellent long-term stability (to be hardly crystallized). Even in the case where the chiral agent has a large HTP, it may be unsuitable for industrial use when it has a complicated structure, since the preparation is not easy and thus the cost is raised. The polymer is required to have an excellent balance as requested in characteristics such as mechanical strength, coating property, solubility, degree of crystallinity, shrinkage, water permeability, gas permeability, melting point, glass transition temperature, thermal resistance and chemical resistance.

Polymerizable oxetane derivatives are disclosed in JP H08-020641 A (1996), (patent document 1), JP 2009-120522 A (patent document 2) and Journal of Materials Chemistry, 2002, 12, 2225-2230 (non-patent document 1). Now, the development of a new oxetane derivative is desired.

SUMMARY OF THE INVENTION

The invention concerns a compound represented by formula (1) below, a composition, a polymer and their use:

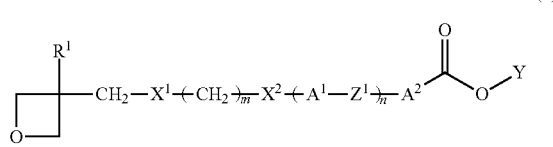

(1)

wherein $R^1$ is hydrogen, methyl or ethyl; $X^1$ is a single bond, —O— or —OCO—; $X^2$ is a single bond, —O—, —COO— or —OCO—; $A^1$ and $A^2$ are each independently a divalent aromatic ring or a divalent cyclohexane ring, and in these rings, arbitrary hydrogen may be replaced by halogen, alkyl having 1 to 3 carbons or halogenated alkyl having 1 to 3 carbons; $Z^1$ is independently a single bond, —O—, —S—, —COO—, —OCO—, —CH$_2$O—, —OCH$_2$—, —CH=CH—COO—, —OCO—CH=CH—, —CH$_2$CH$_2$—COO—, —OCO—CH$_2$CH$_2$—, —CON(R)— or —N(R)CO—; R is hydrogen or methyl; Y is a terpenoid residue or a steroid residue; m is an integer from 0 to 20 and n is an integer from 0 to 3.

DETAILED DESCRIPTION OF THE INVENTION

An advantage of the invention is to provide a polymerizable and optically active compound which has a high polymerizability, a large HTP (helical twist power), a small temperature dependency of the HTP, an excellent compatibility with another liquid crystal material, an easy adjustment of characteristics that are required as a cholesteric material, and synthesized in an economical way suitable for an industrial scale.

The compound of the invention can be suitably used as a chiral agent, since the polymerizability is high, the HTP is large, the temperature dependency of the HTP is small, the compatibility with another liquid crystal material is excellent, the adjustment of characteristics that is required as a cholesteric material is easy, and the compound can be synthesized in an economical method that is suitable for an industrial scale. Incidentally, the liquid crystal material is the general term of the component which is contained in the liquid crystal composition except the liquid crystal compound which is shown by the following formula (1).

The invention includes the following items.

[1] A compound represented by the following formula (1).

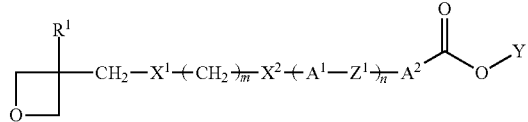
(1)

In the formula (1), $R^1$ is hydrogen, methyl or ethyl; $X^1$ is a single bond, —O— or —OCO—; $X^2$ is a single bond, —O—, —COO— or —OCO—; $A^1$ and $A^2$ are each independently a divalent aromatic ring or a divalent cyclohexane ring, and in these rings, arbitrary hydrogen may be replaced by halogen, alkyl having 1 to 3 carbons or halogenated alkyl having 1 to 3 carbons; $Z^1$ is independently a single bond, —O—, —S—, —COO—, —OCO—, —CH$_2$O—, —OCH$_2$—, —CH=CH—COO—, —OCO—CH=CH—, —CH$_2$CH$_2$—COO—, —OCO—CH$_2$CH$_2$—, —CON(R)— or —N(R)CO—; R is hydrogen or methyl; Y is a terpenoid residue or a steroid residue; m is an integer from 0 to 20; and n is an integer from 0 to 3.

[2] The compound according to [1], wherein the terpenoid residue is a residue of menthol, neomenthol, isomenthol, carveol, dihydrocarveol, terpinen-4-ol, verbenol, nopol, perillyl alcohol, cedrol, citronellol, dihydrocitronellol or isopinocampheol; and the steroid residue is a residue of sterol.

[3] The compound according to [2], wherein the sterol residue is a residue of stanol, cholesterol, phytosterol or phytostanol.

[4] The compound according to [1], wherein in the formula (1), Y is a menthol residue or a cholesterol residue.

[5] The compound according to [1], wherein in the formula (1), -($A^1$-$Z^1$)$_n$-$A^2$- is a divalent group represented by the following formula (2-1) or (2-2).

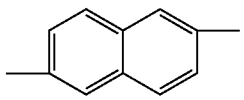
(2-1)

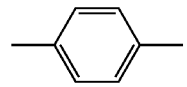
(2-2)

[6] The compound according to [1], wherein in the formula (1), -($A^1$-$Z^1$)$_n$-$A^2$- is a divalent group represented by any one of the following formulas (3-1) to (3-7).

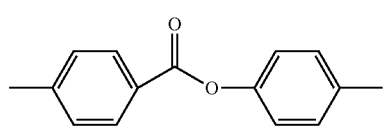
(3-1)

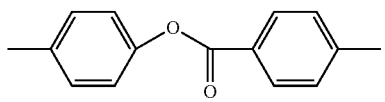
(3-2)

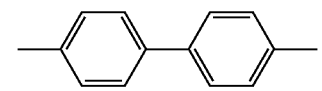
(3-3)

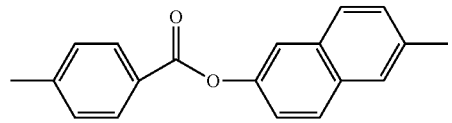
(3-4)

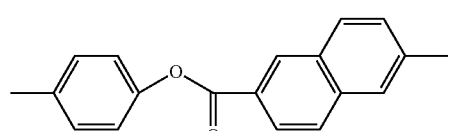
(3-5)

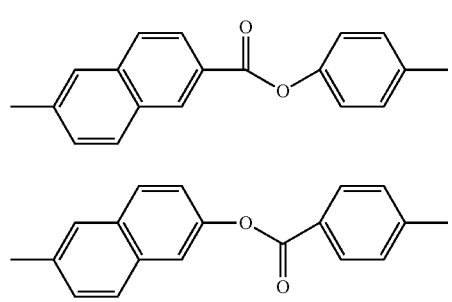
(3-6)

(3-7)

[7] The compound according to [1], wherein in the formula (1), -($A^1$-$Z^1$)$_n$-$A^2$- is a divalent group represented by any one of the following formulas (4-1) to (4-8).

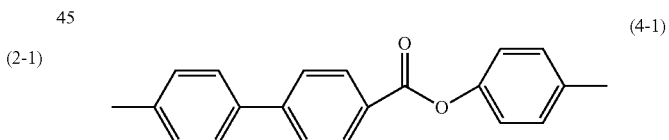
(4-1)

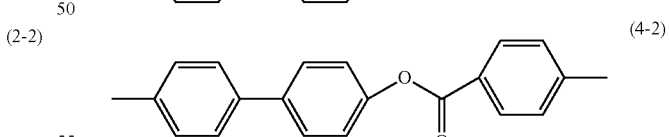
(4-2)

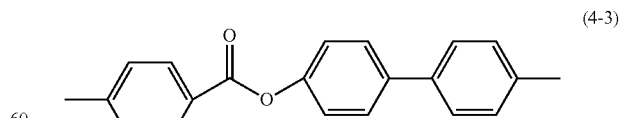
(4-3)

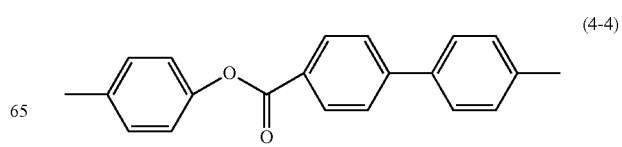
(4-4)

(4-5)
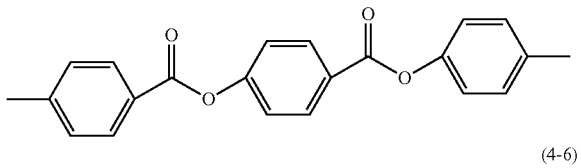

(4-6)
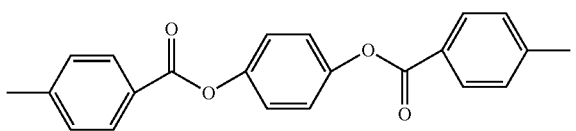

(4-7)
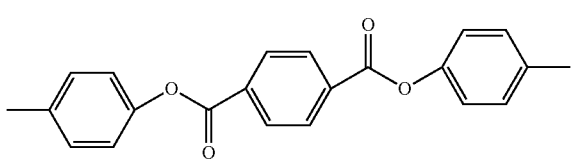

(4-8)
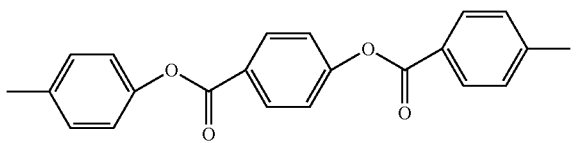

[8] The compound according to [1], wherein in the formula (1), $-(A^1-Z^1)_n-A^2-$ is the following formula (3-1) and $X^1$ is —O—.

(3-1)
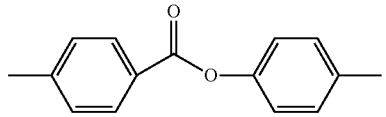

[9] A liquid crystal composition, including the compound according to any one of [1] to [8] and a liquid crystal compound.
[10] The liquid crystal composition according to [9], wherein the composition includes at least one polymerizable liquid crystal compound as the liquid crystal compound.
[11] A polymer formed by polymerization of the liquid crystal composition according to [10].
[12] The polymer according to [11], wherein the polymer exhibits a cholesteric phase.
[13] Use of the liquid crystal composition according to [9] or [10] for application selected from liquid crystal pigments, coating materials, spray inks, printing inks, cosmetics, anti-counterfeit printed matters, ornaments and optical films.
[14] Use of the polymer according to [11] or [12] for application selected from liquid crystal pigments, coating materials, spray inks, printing inks, cosmetics, anti-counterfeit printed matters, ornaments and optical films.

Hereinafter, the compound and its use according to the invention will be explained in detail. The compound represented by formula (1) may be abbreviated to "the compound (1)." When n is 2 or 3 in the formula (1), this compound has a plurality of $A^1$. In this case, arbitrary two $A^1$ may be the same substituents or different substituents. The same rule applies to $Z^1$. The same rule applies to other formulas.

[Compounds]
Since the compound (1) of the invention has such a structure shown in formula (1) described above, it can be used as a chiral agent which has a high polymerizability, a large HTP, a small temperature dependency of the HTP, an excellent compatibility with another liquid crystal material, and an easy adjustment of characteristics to a cholesteric material required.

The compound (1) has an oxetane moiety at one of the terminals, and a terpenoid residue or a steroid residue at the other terminal, and thus it exhibits characteristics such as a high polymerizability, a suitable optical activity and an excellent compatibility. Here, when "compound (1) exhibits a suitable optical activity", it means that compound (1) has an appropriate range of HTP for a purpose.

In the formula (1), $R^1$ is hydrogen, methyl or ethyl. Desirable $R^1$ is ethyl. $X^1$ is a single bond, —O— or —OCO—. Desirable $X^1$ is —O—. $X^2$ is a single bond, —O—, —COO— or —OCO—. Desirable $X^2$ is —O—.

In the formula (1), $A^1$ and $A^2$ are each independently a divalent aromatic ring or a divalent cyclohexane ring, and in these rings, arbitrary hydrogen may be replaced by halogen, alkyl having 1 to 3 carbons or halogenated alkyl having 1 to 3 carbons.

The aromatic ring may be a monocyclic ring such as benzene, a condensed aromatic ring such as naphthalene and anthracene, and a hetero-aromatic ring including a hetero atom such as oxygen and nitrogen, such as furan and pyrimidine.

Examples of $A^1$ and $A^2$ include 1,4-cyclohexylene, 1,3-phenylene, 1,4-phenylene and naphthalene-2,6-diyl. Desirable $A^1$ or $A^2$ is 1,4-phenylene and naphthalene-2,6-diyl.

Halogen may be any one of fluorine, chlorine, bromine and iodine. Desirable halogen is fluorine. Halogenated alkyl is alkyl in which arbitrary hydrogen is replaced by halogen, and desirable halogenated alkyl is fluoromethyl and trifluoromethyl.

In the formula (1), $Z^1$ is a single bond, —O—, —S—, —COO—, —OCO—, —CH$_2$O—, —OCH$_2$—, —CH=CH—COO—, —OCO—CH=CH—, —CH$_2$CH$_2$—COO—, —OCO—CH$_2$CH$_2$—, —CON(R)— or —N(R)CO—; and R is hydrogen or methyl. Desirable $Z^1$ is a single bond, —COO— and —OCO—, and more desirable $Z^1$ is —COO—.

In the formula (1), Y is a terpenoid residue or a steroid residue. The terpenoid residue includes, but is not limited to, a residue of terpenoid alcohol such as menthol, neomenthol, isomenthol, carveol, dihydrocarveol, terpinen-4-ol, verbenol, nopol, perillyl alcohol, cedrol, citronellol, dihydrocitronellol and isopinocampheol. A desirable terpenoid residue is a menthol residue in view of availability, mass productivity, economic efficiency and so forth.

The steroid residue includes, but is not limited to, a residue of sterol, and so forth. The sterol residue includes stanol, cholesterol, phytosterol, phytostanol, and the like. A desirable sterol residue is a cholesterol residue in view of availability, mass productivity, and so forth.

In the formula (1), m is an integer from 0 to 20, and desirable m is an integer from 2 to 6. Incidentally, at least one of $X^1$ and $X^2$ is a single bond when m is 0.

In the formula (1), n is an integer from 0 to 3, desirable n is an integer from 0 to 2, and more desirable n is 1 or 2.

In the formula (1), desirable examples of a moiety represented by $-(A^1-Z^1)_n-A^2-$ are
(i) a divalent group represented by the formula (2-1) or (2-2) described above when n is 0;
(ii) any one of divalent groups represented by the formulas (3-1) to (3-7) described above when n is 1; and (iii) any one of divalent groups represented by the formulas (4-1) to (4-8) described above when n is 2.

The compound which has a large HTP and a quite excellent compatibility with another liquid crystal material can be provided when a moiety represented by -($A^1$-$Z^1$)$_n$-$A^2$ is a divalent group of (i) to (iii) described above.

In the formula (1) described above, any combination of the divalent group represented by -($A^1$-$Z^1$)$_n$-$A^2$- and $X^1$ are desirable, and it is more desirable that the divalent group represented by -($A^1$-$Z^1$)$_n$-$A^2$- is the formula (3-1) and $X^1$ is —O—. The compound which has quite excellent compatibility with another liquid crystal material can be provided by this combination.

Examples of the method for the synthesis of the compound (1) of the invention will be explained below. The compound (1) can be synthesized according to the following synthetic schemes I to IV. $R^1$, $A^1$, $Z^1$, $A^2$, Y, m and n in the following schemes have the same meaning with those of $R^1$, $A^1$, $Z^1$, $A^2$, Y, m and n in the formula (1) described above, respectively.

(I) The compound in which $X^1$ is —O—, $X^2$ is —O—, and $Z^1$ that is the closest to the oxetane moiety is —COO— in the formula (1) is synthesized according to the following synthetic scheme.

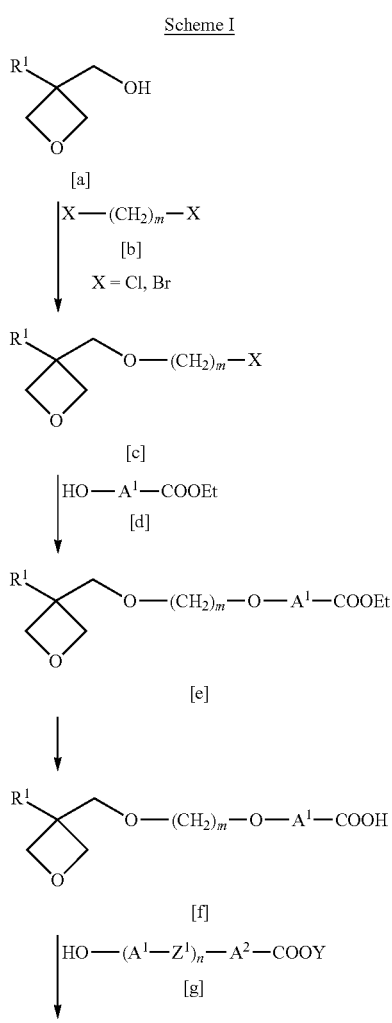

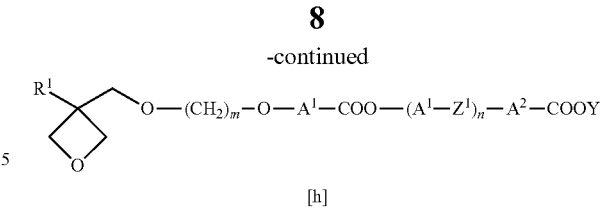

As Scheme I shows, first, etherification of the alcohol [a] with the halide [b] in the presence of a base gives the halide [c]. Examples of the base include calcium hydroxide, sodium hydroxide, potassium carbonate and sodium hydride. Next, etherification of the halide [c] with the alcohol [d] in the presence of a base gives the ester [e]. Then, hydrolysis of the ester [e] gives the carboxylic acid [f], and the carboxylic acid [f] is reacted with the alcohol [g] to give the objective oxetane derivative [h]. Incidentally, "Et" in the scheme stands for ethyl.

(II) In the formula (1), the compound in which $X^1$ is —O—, $X^2$ is —O—, and $Z^1$ that is the closest to the oxetane moiety is —OCH$_2$— is synthesized according to the following synthetic scheme.

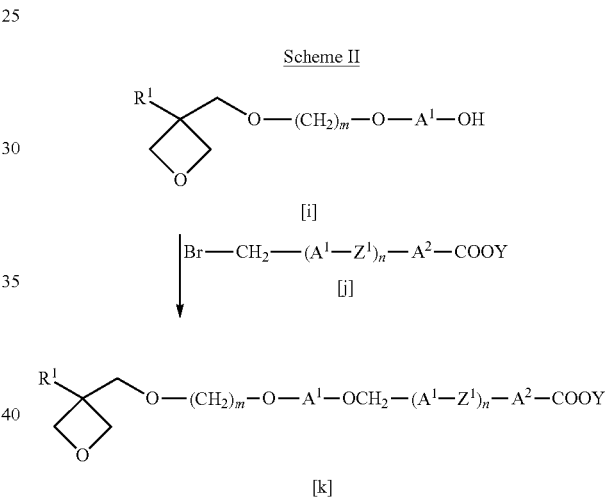

The alcohol [i] shown in Scheme II is synthesized by the method described in Macromolecules, Vol. 28, pages 1673 to 1680 (1995), and so forth. The oxetane derivative [k] is synthesized by etherification of the alcohol [i] with bromide [j].

(III) In the formula (1), the compound in which $X^1$ is —O—, $X^2$ is —O—, and $Z^1$ that is the closest to the oxetane moiety is a single bond is synthesized according to the following synthetic scheme.

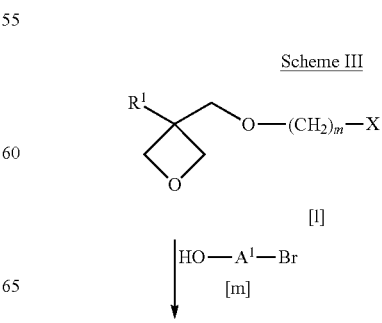

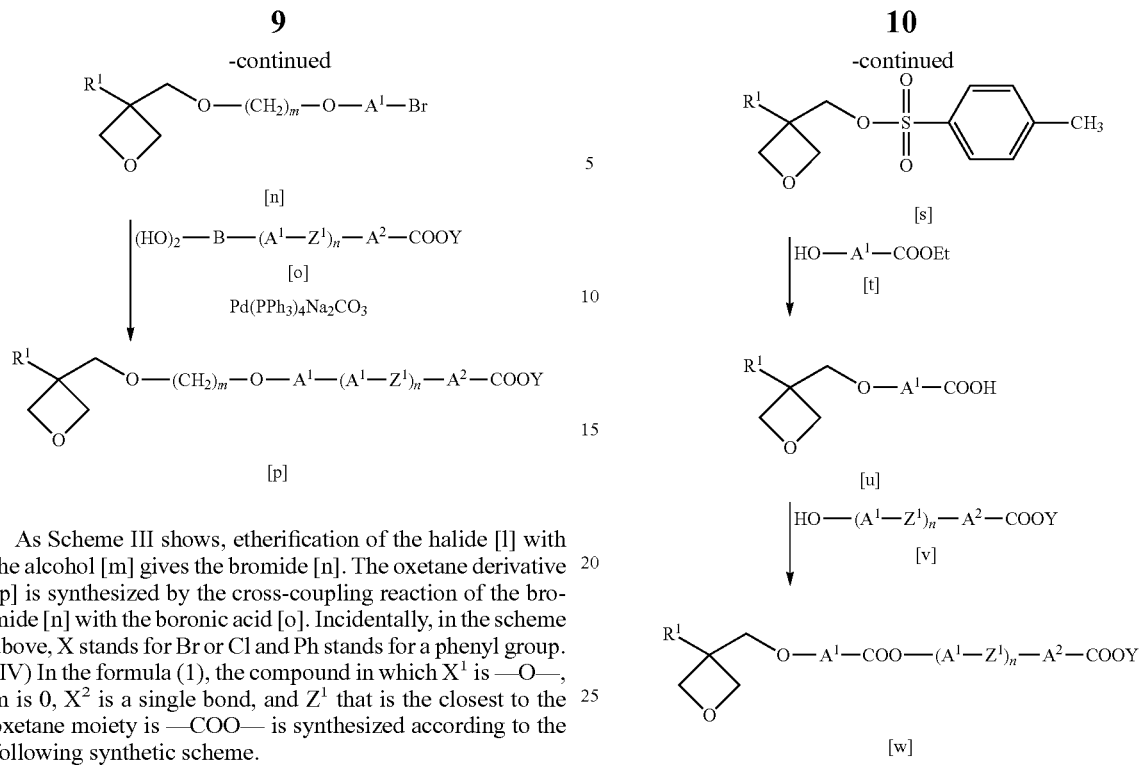

As Scheme III shows, etherification of the halide [l] with the alcohol [m] gives the bromide [n]. The oxetane derivative [p] is synthesized by the cross-coupling reaction of the bromide [n] with the boronic acid [o]. Incidentally, in the scheme above, X stands for Br or Cl and Ph stands for a phenyl group. (IV) In the formula (1), the compound in which $X^1$ is —O—, m is 0, $X^2$ is a single bond, and $Z^1$ that is the closest to the oxetane moiety is —COO— is synthesized according to the following synthetic scheme.

As Scheme IV shows, the tosylation of the alcohol [q] with p-toluene sulfonyl chloride [r] in the presence of a base such as pyridine gives the tosylate [s]. Etherification of the tosylate [s] with the alcohol [t] and hydrolysis of the product gives the carboxylic acid [u]. The oxetane derivative [w] is synthesized by dehydration reaction of the carboxylic acid [u] and the alcohol [v]. Incidentally, "Et" in the scheme stands for ethyl.

The compounds (1-1) to (1-160) can be synthesized by a general synthetic method shown in Schemes I to IV. Structures of compounds thus synthesized can be confirmed by means of, for example, proton-NMR spectroscopy.

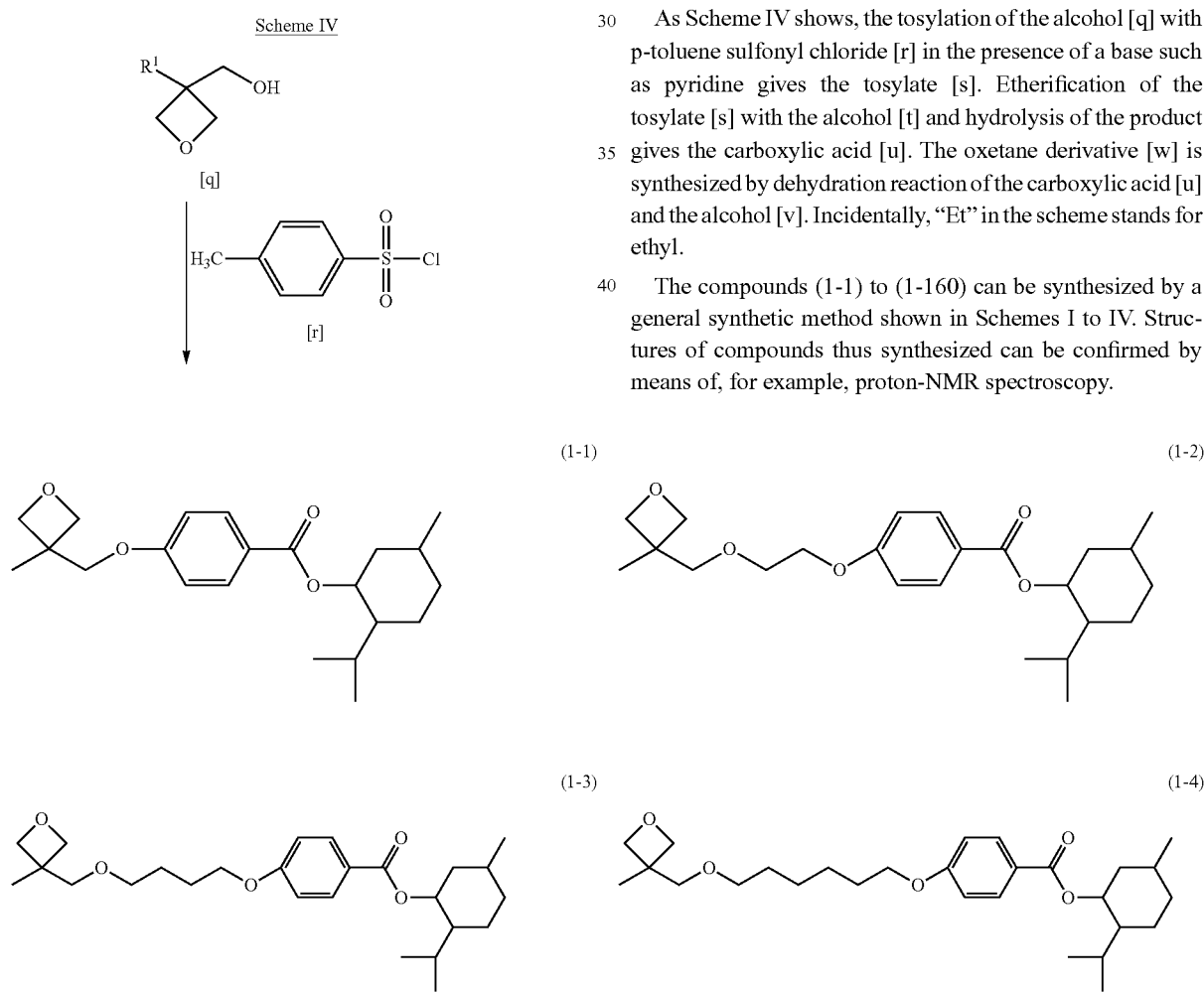

-continued
(1-5)
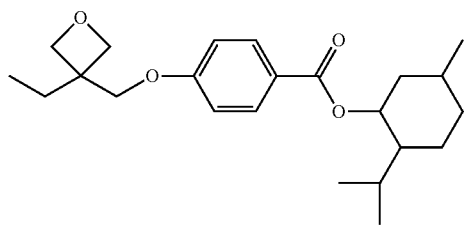
(1-6)
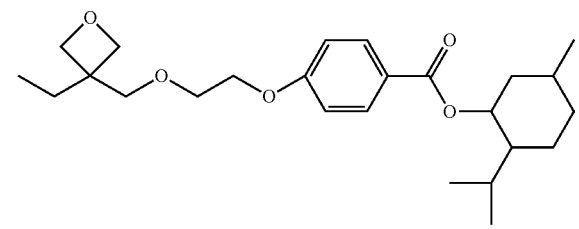
(1-7)
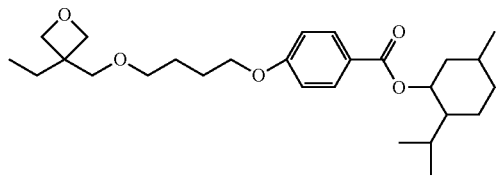
(1-8)
(1-9)
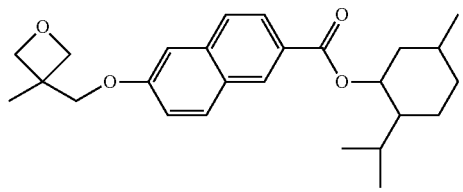
(1-10)
(1-11)
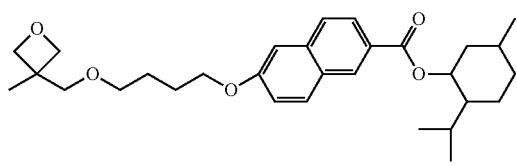
(1-12)
(1-13)
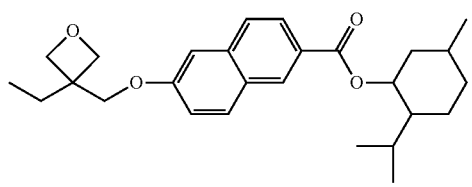
(1-14)
(1-15)
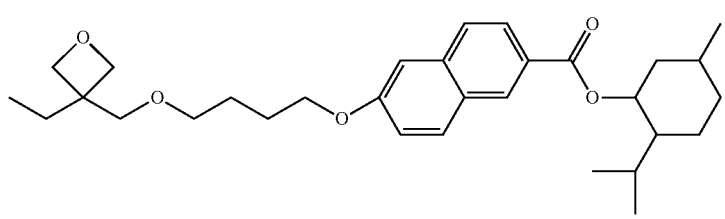
(1-16)
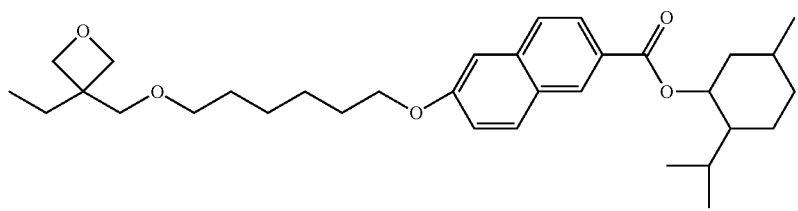

(1-17)
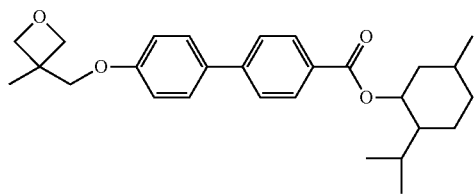
(1-18)
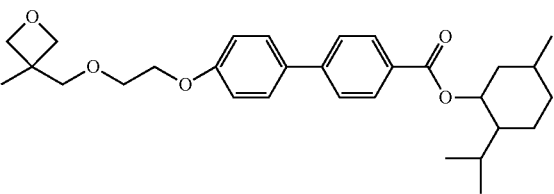
(1-19)
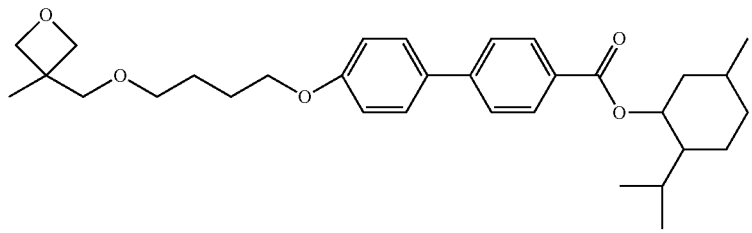
(1-20)
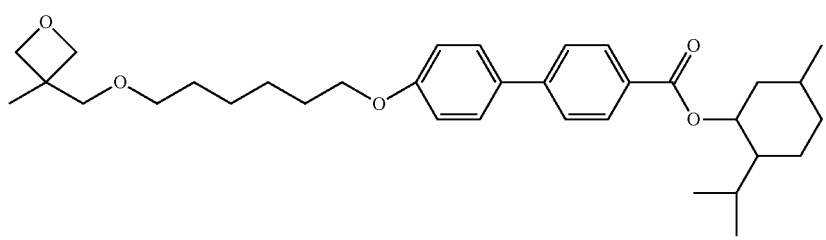
(1-21)
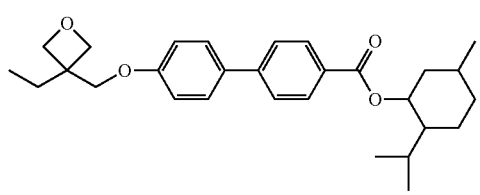
(1-22)
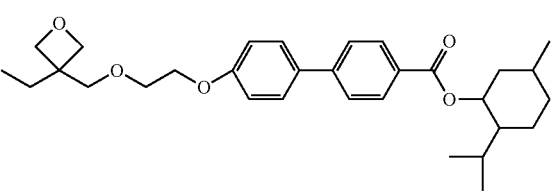
(1-23)
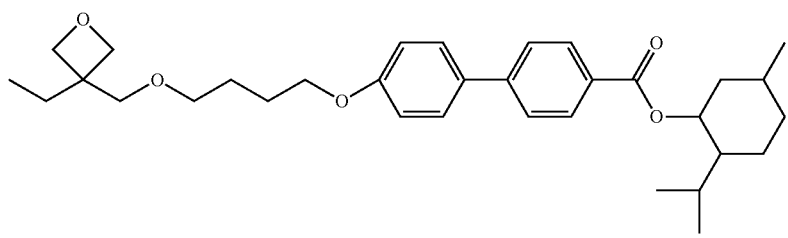
(1-24)
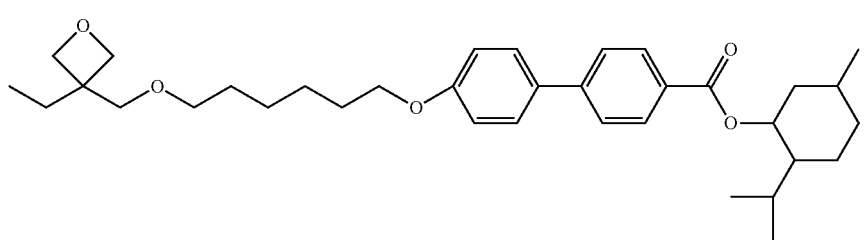
(1-25)
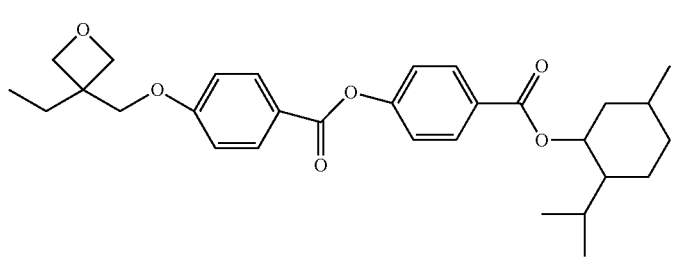

-continued
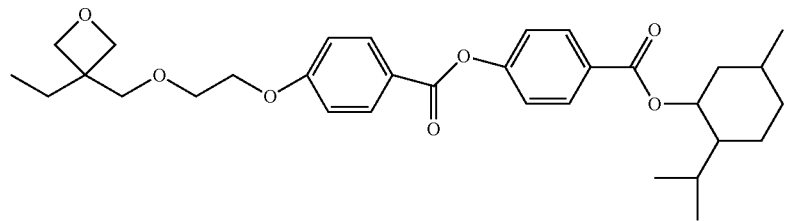
(1-26)
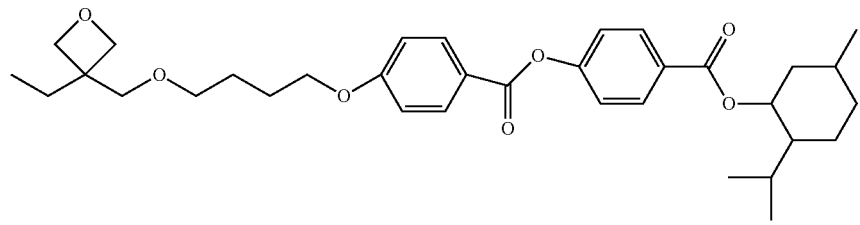
(1-27)
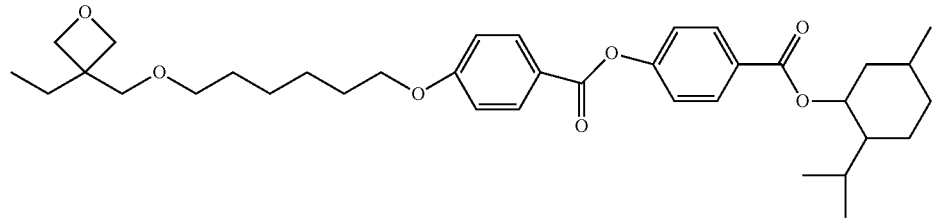
(1-28)
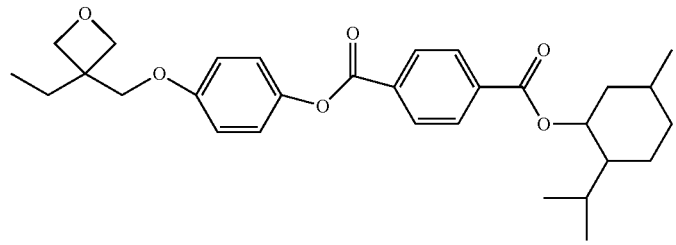
(1-29)
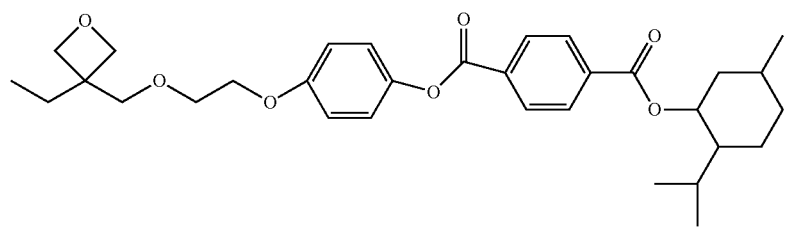
(1-30)
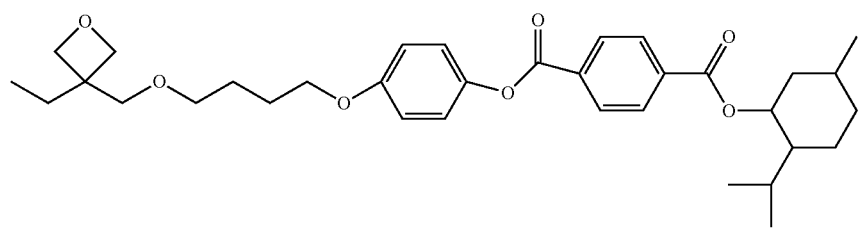
(1-31)
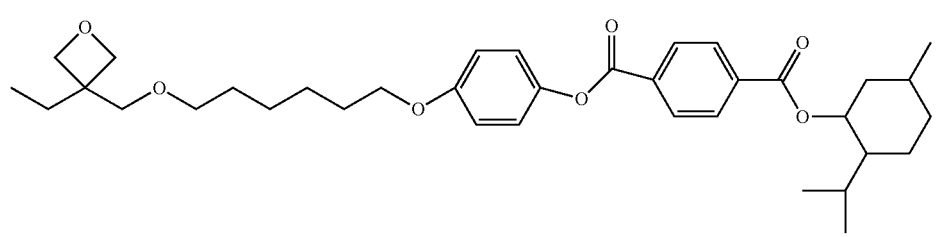
(1-32)

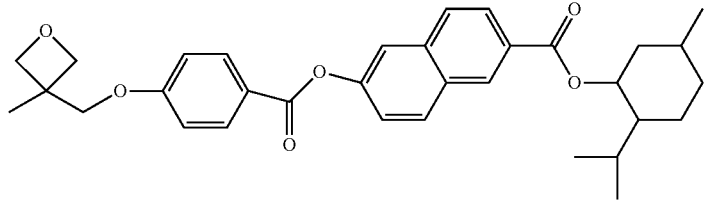
(1-33)
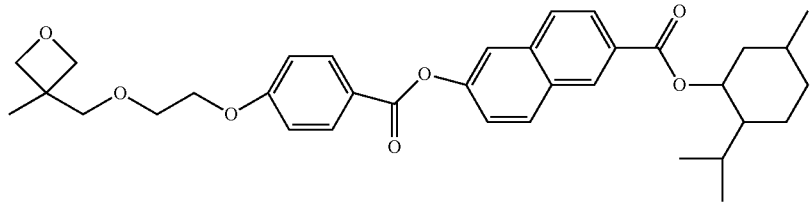
(1-34)
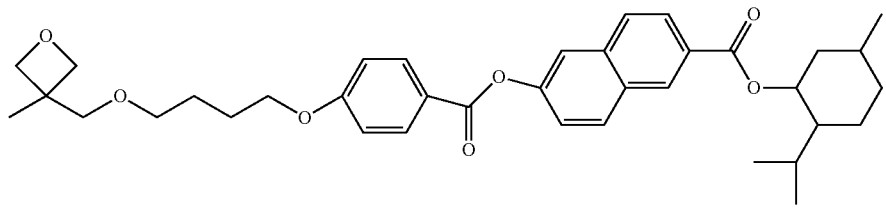
(1-35)
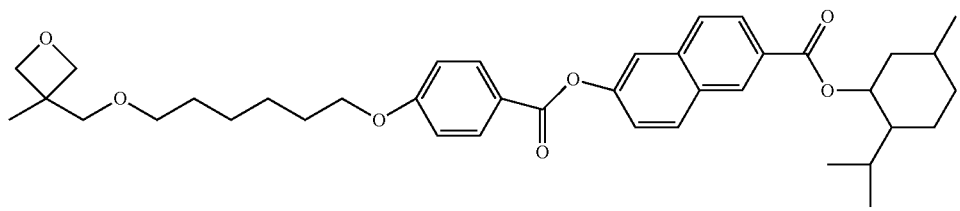
(1-36)
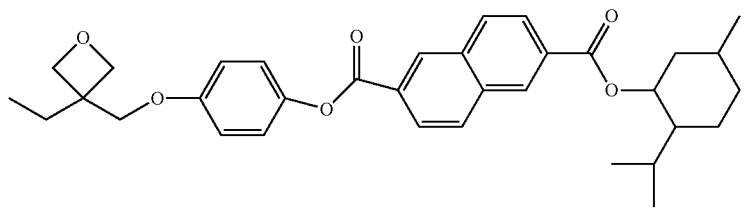
(1-37)
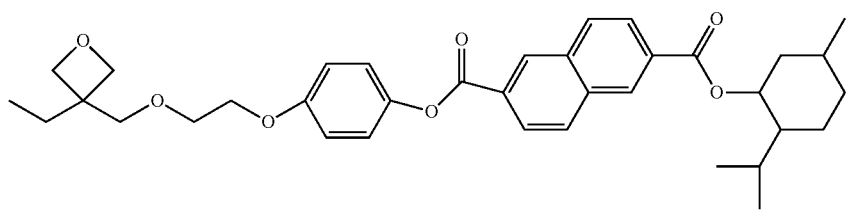
(1-38)
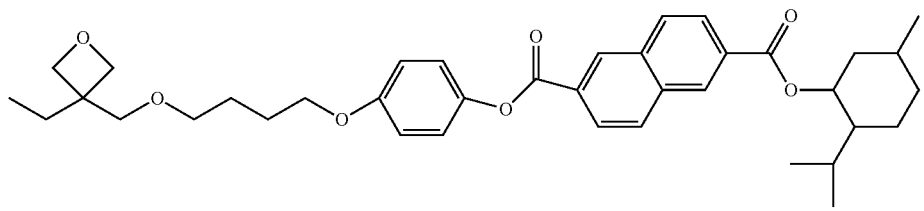
(1-39)

-continued
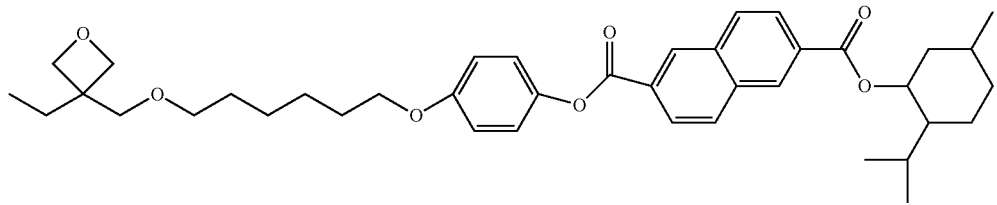
(1-40)
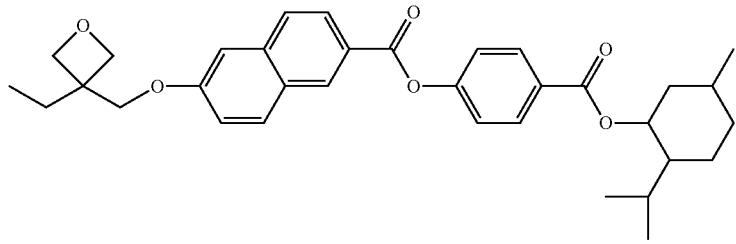
(1-41)
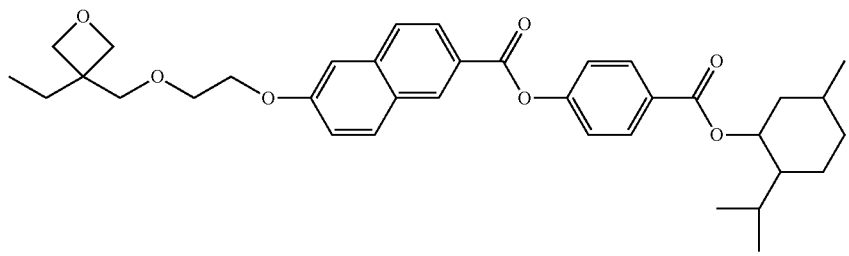
(1-42)
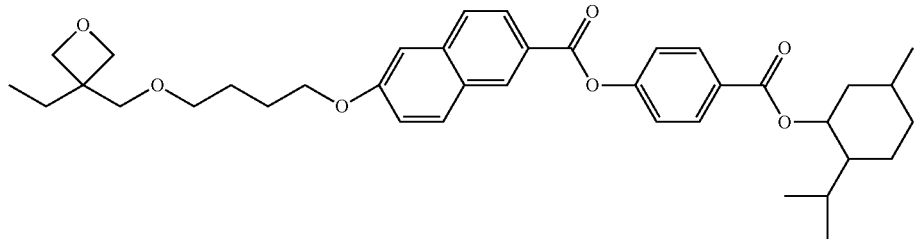
(1-43)
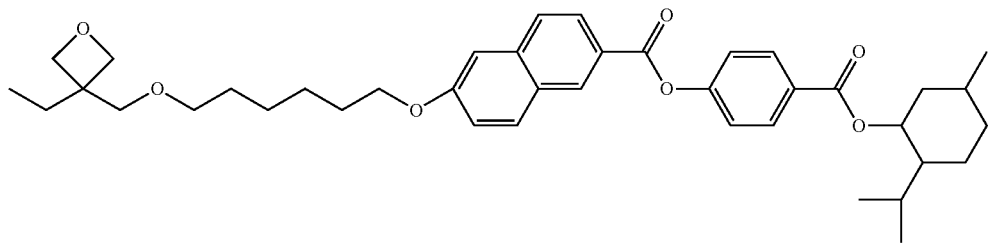
(1-44)
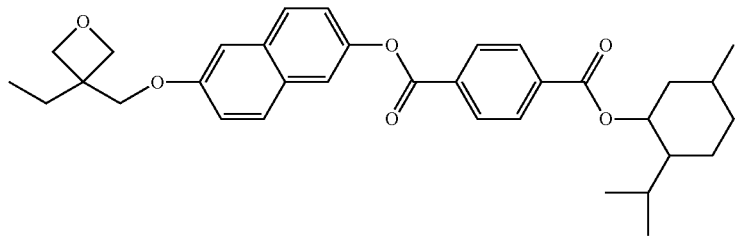
(1-45)

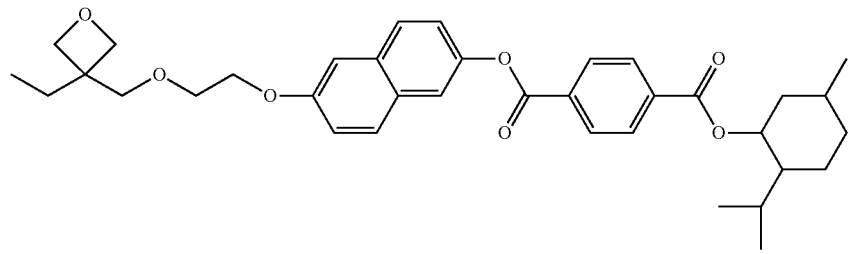
(1-46)
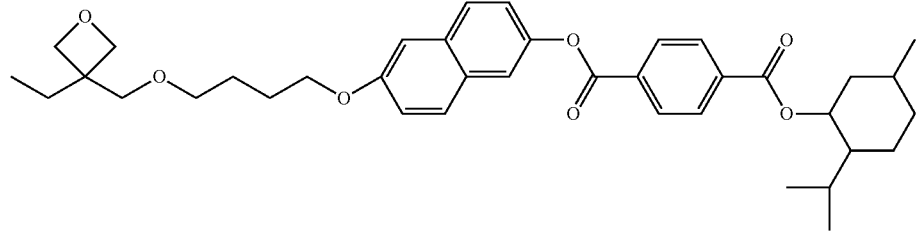
(1-47)
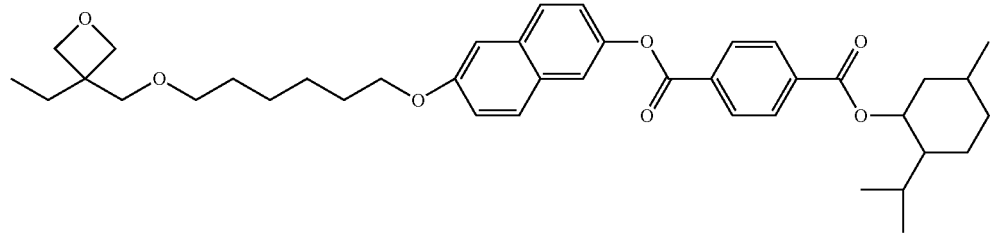
(1-48)
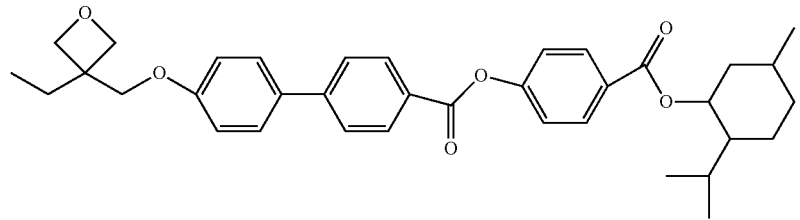
(1-49)
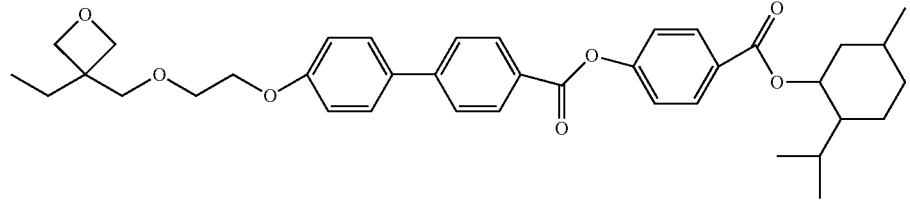
(1-50)
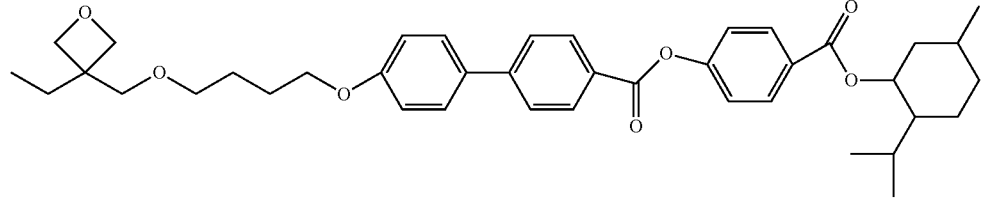
(1-51)
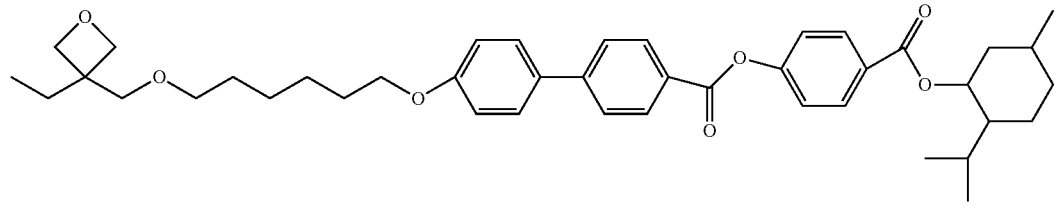
(1-52)

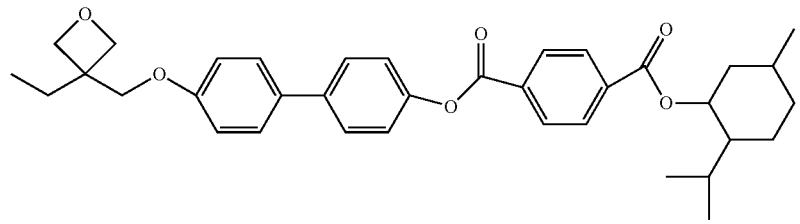
(1-53)
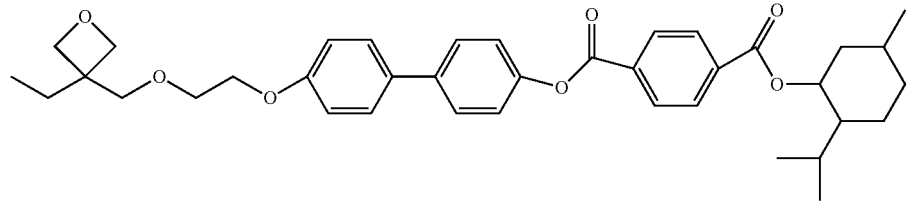
(1-54)
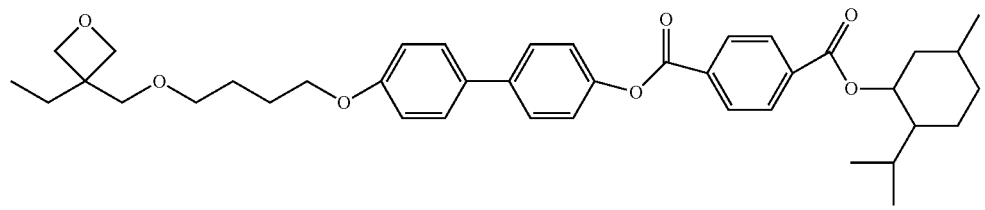
(1-55)
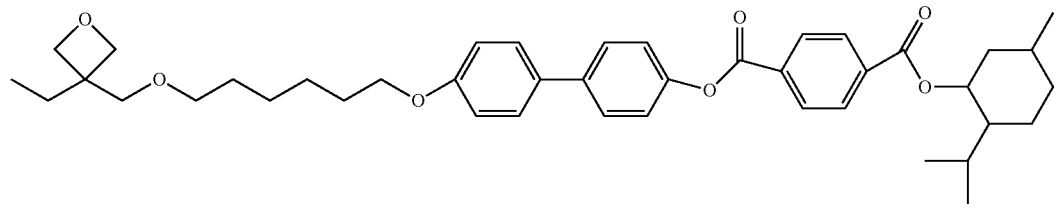
(1-56)
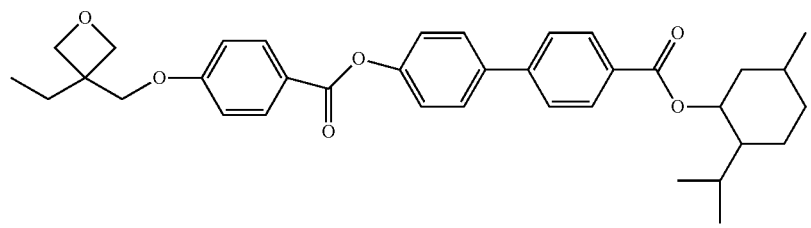
(1-57)
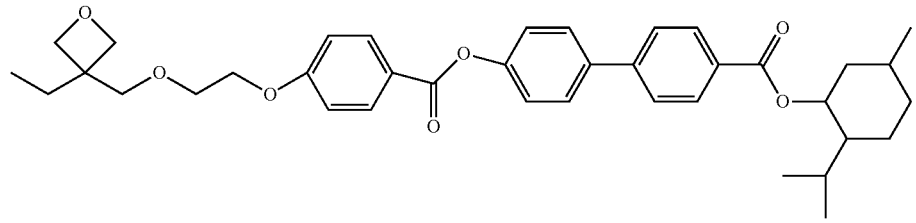
(1-58)
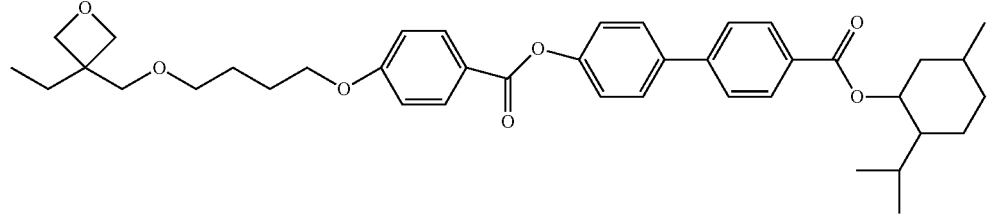
(1-59)

-continued
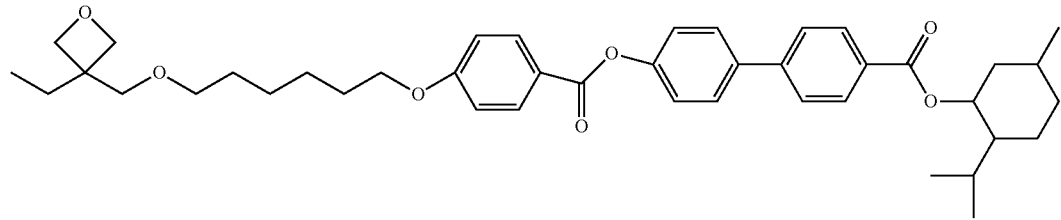
(1-60)
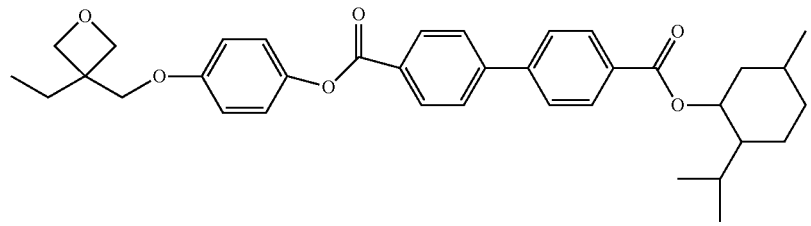
(1-61)
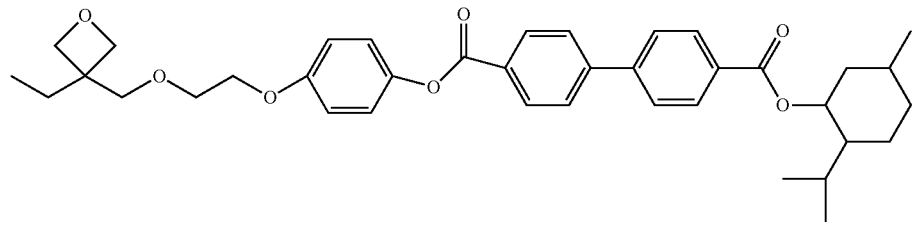
(1-62)
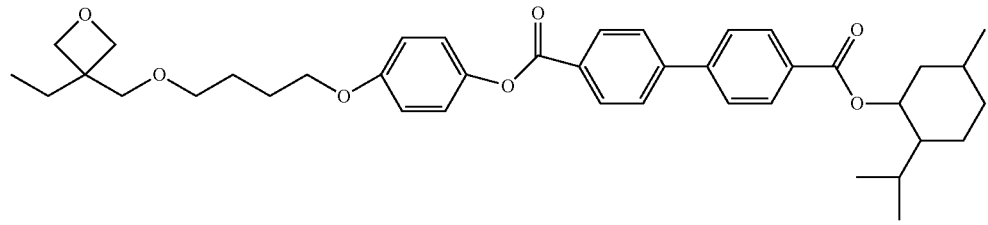
(1-63)
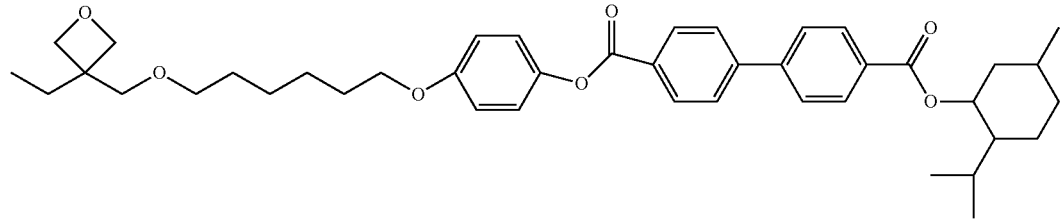
(1-64)
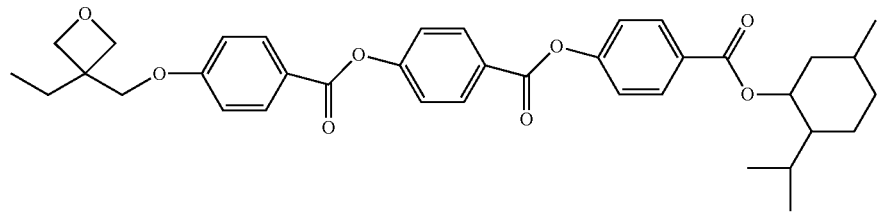
(1-65)
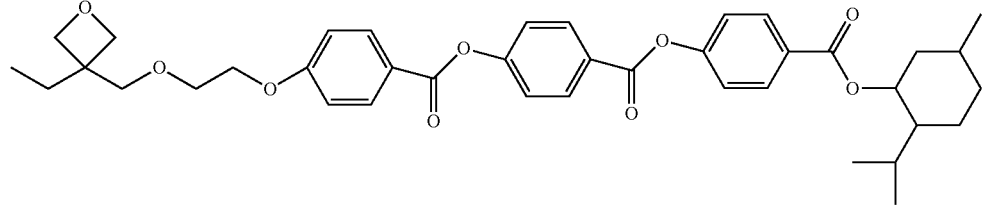
(1-66)

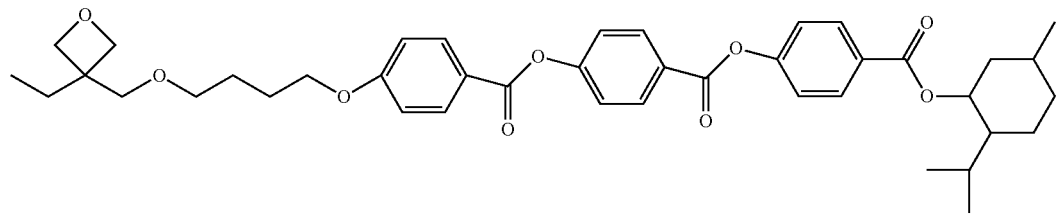
(1-67)
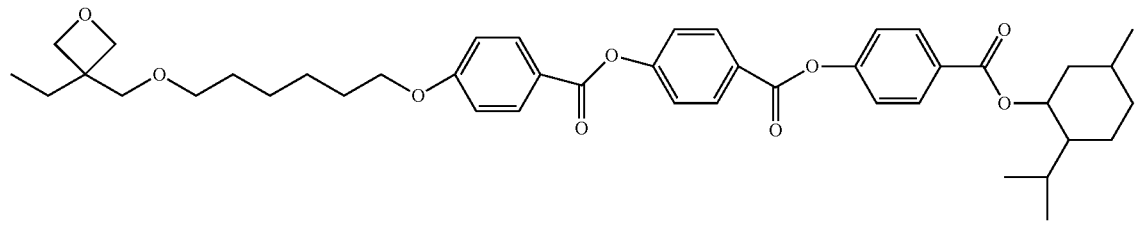
(1-68)
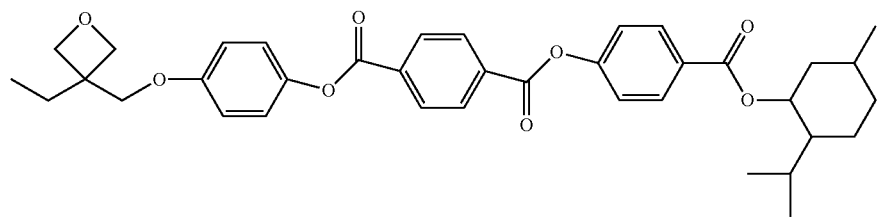
(1-69)
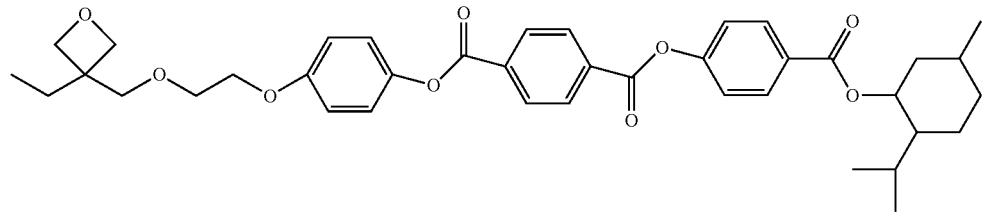
(1-70)
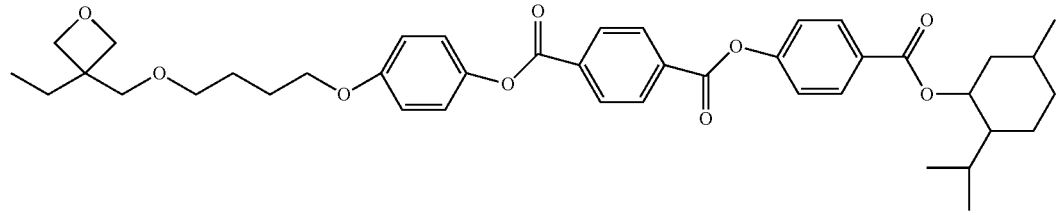
(1-71)
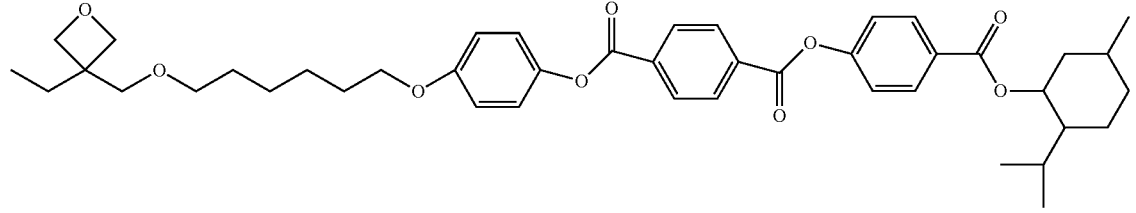
(1-72)
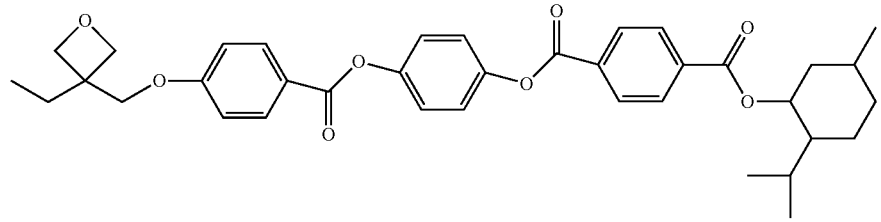
(1-73)

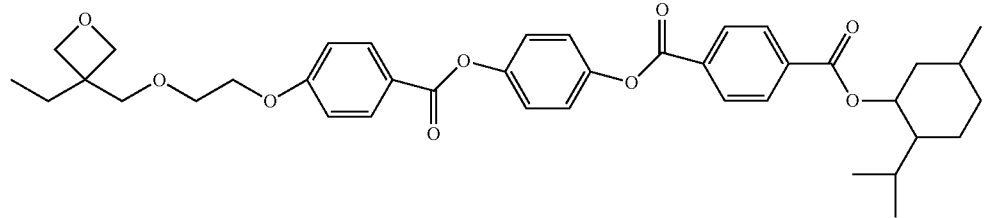
(1-74)
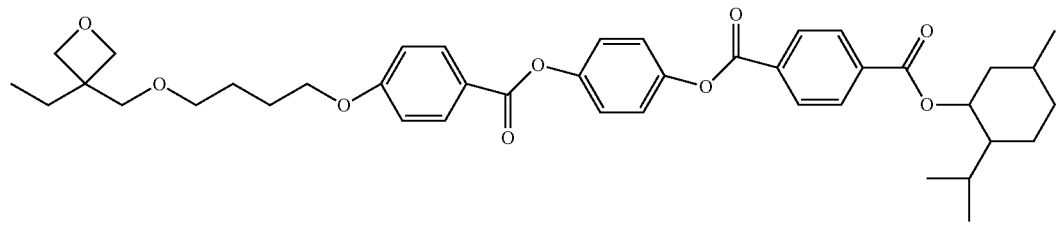
(1-75)
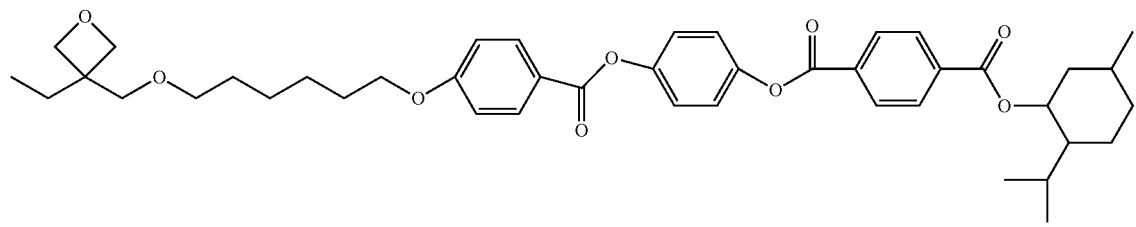
(1-76)
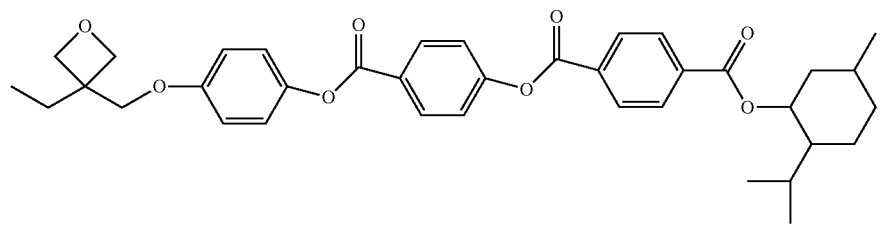
(1-77)
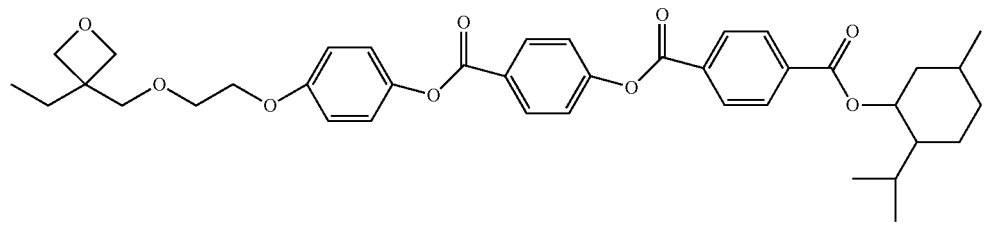
(1-78)
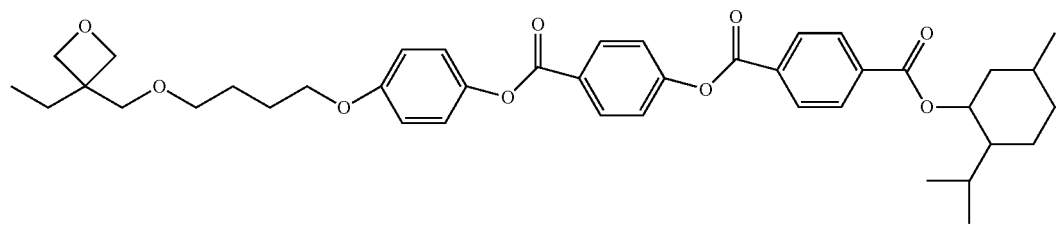
(1-79)
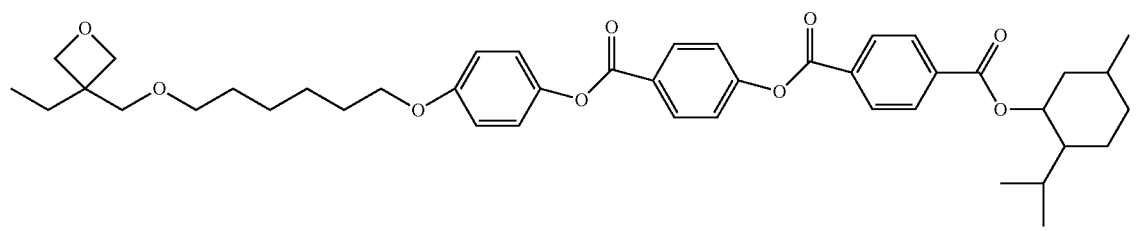
(1-80)

-continued
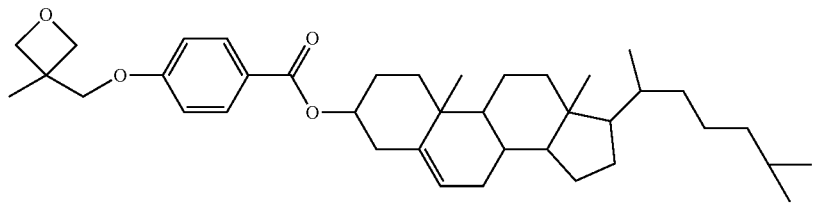
(1-81)
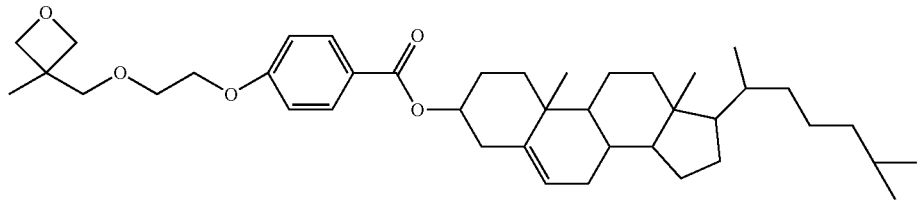
(1-82)
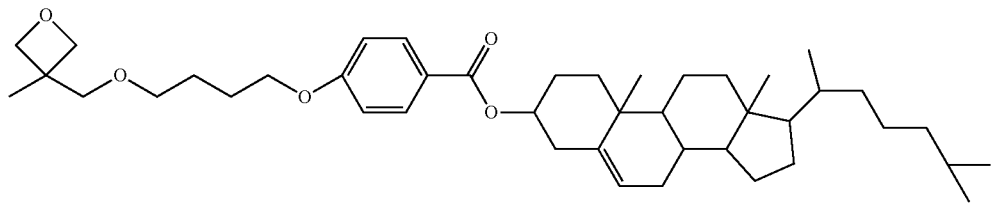
(1-83)
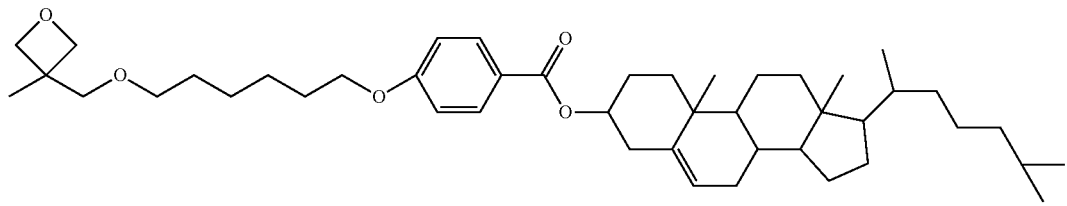
(1-84)
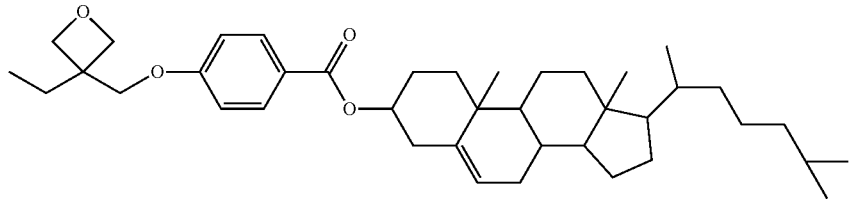
(1-85)
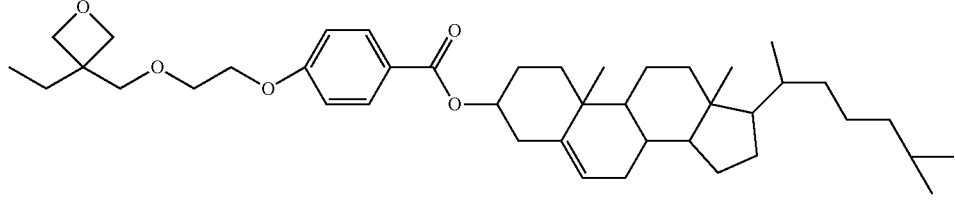
(1-86)
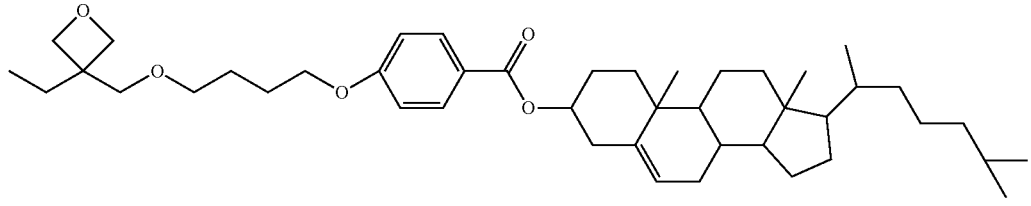
(1-87)

-continued
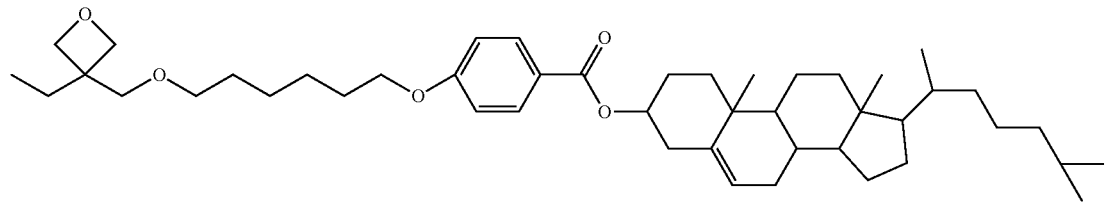
(1-88)
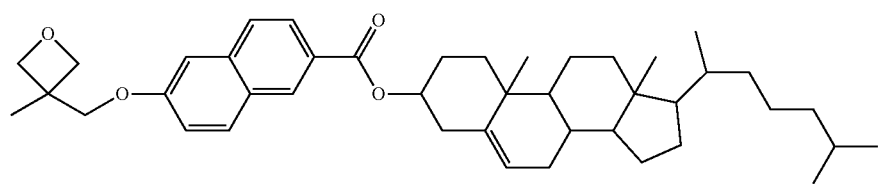
(1-89)
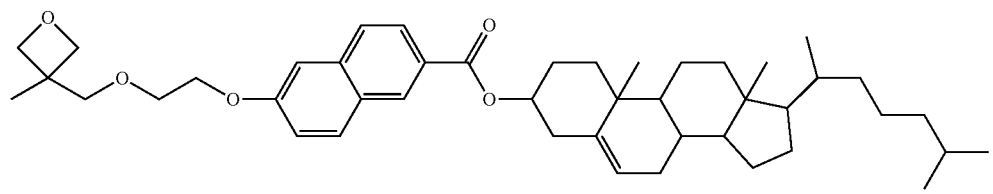
(1-90)
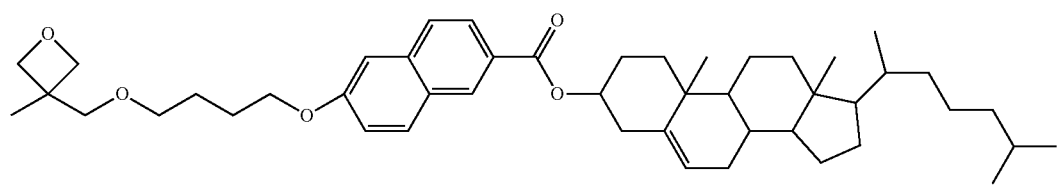
(1-91)
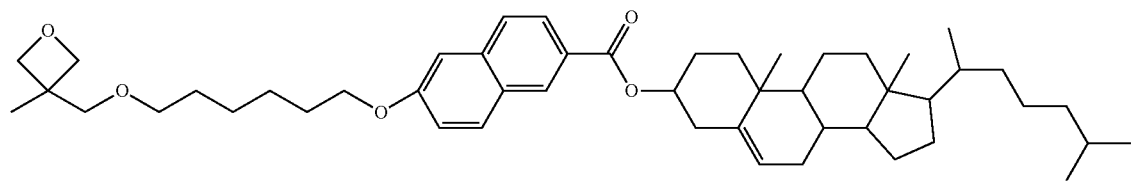
(1-92)
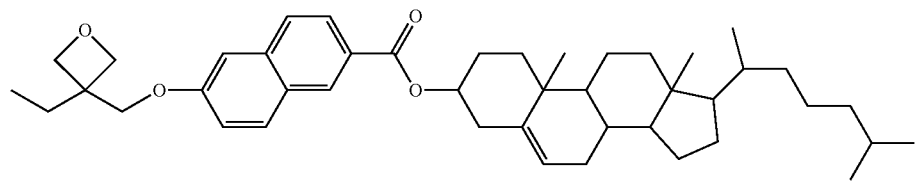
(1-93)
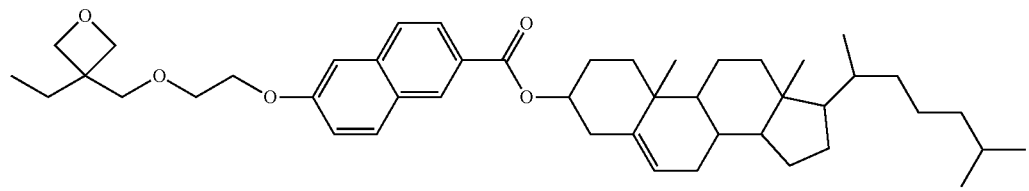
(1-94)
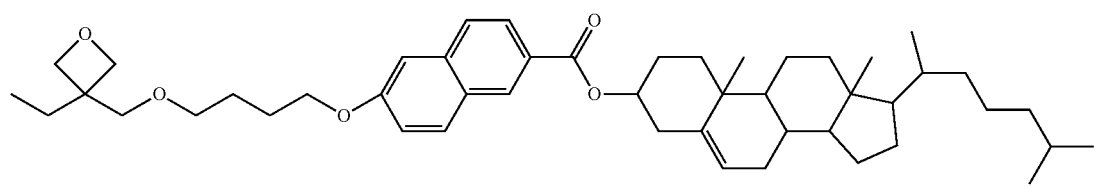
(1-95)

(1-96)
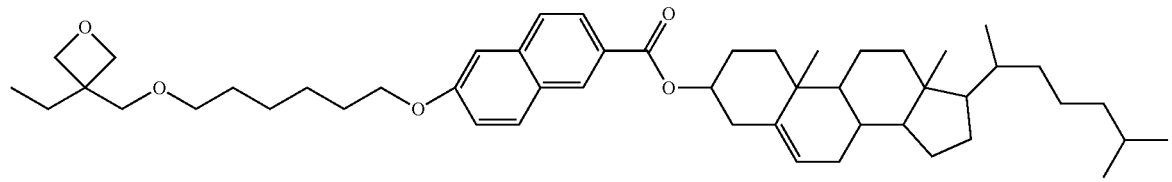
(1-97)
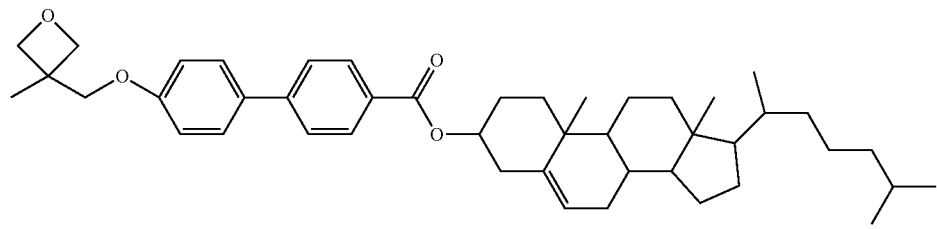
(1-98)
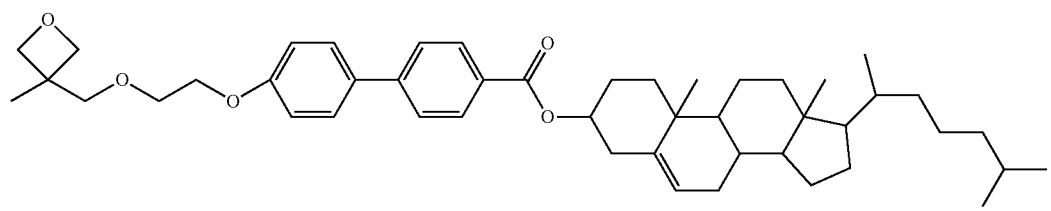
(1-99)
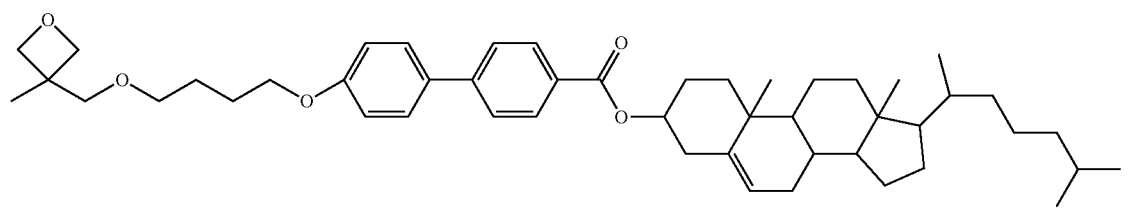
(1-100)
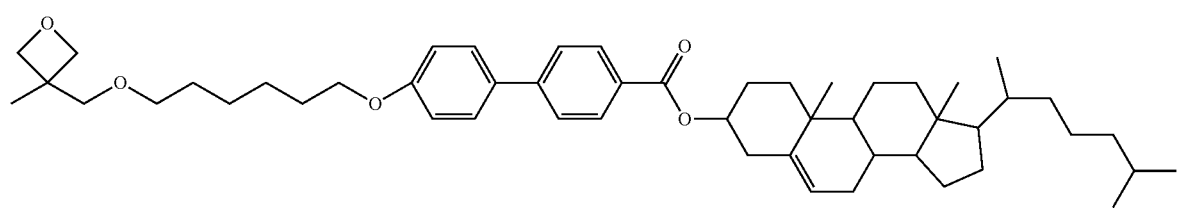
(1-101)
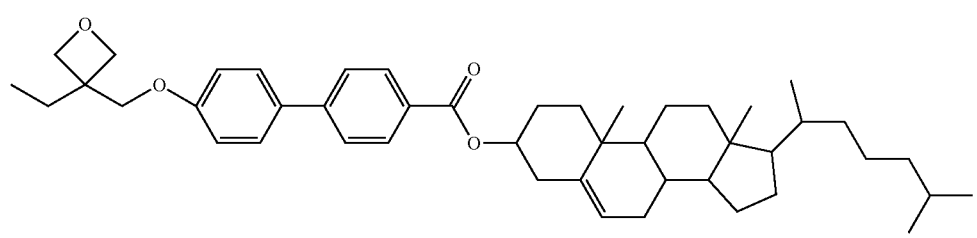
(1-102)
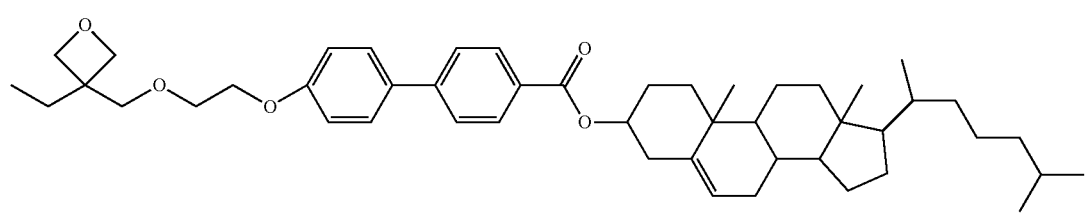

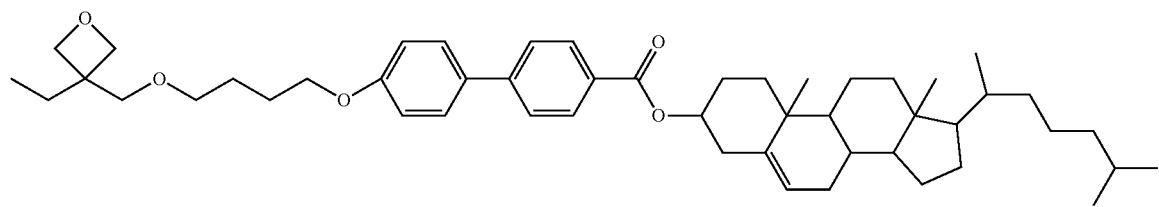
(1-103)
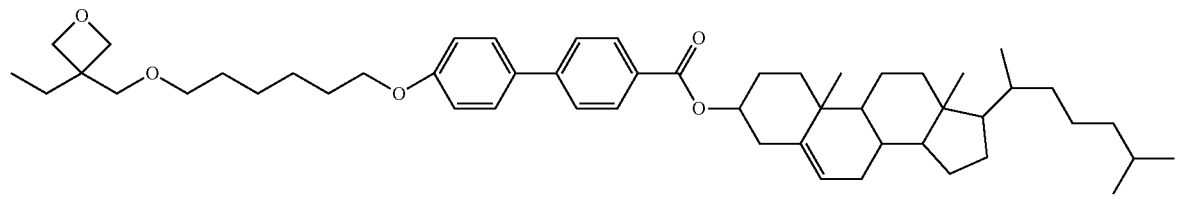
(1-104)
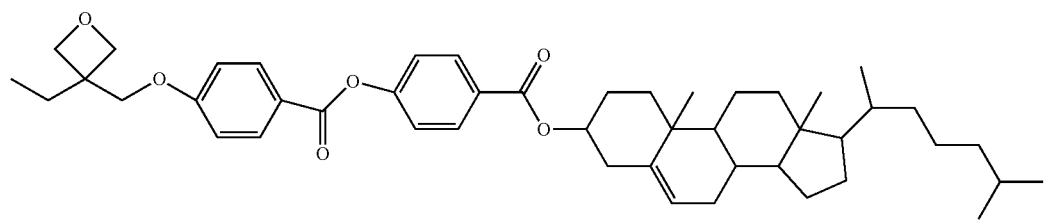
(1-105)
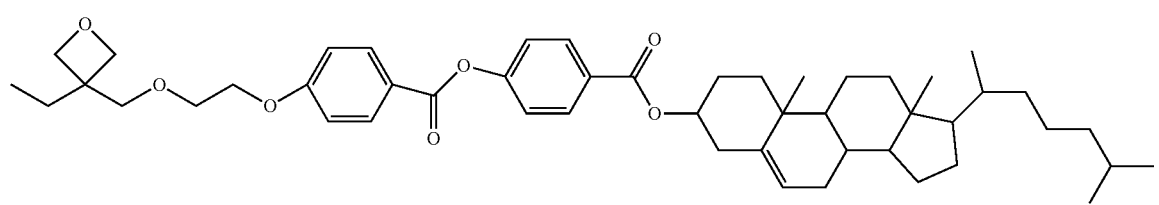
(1-106)
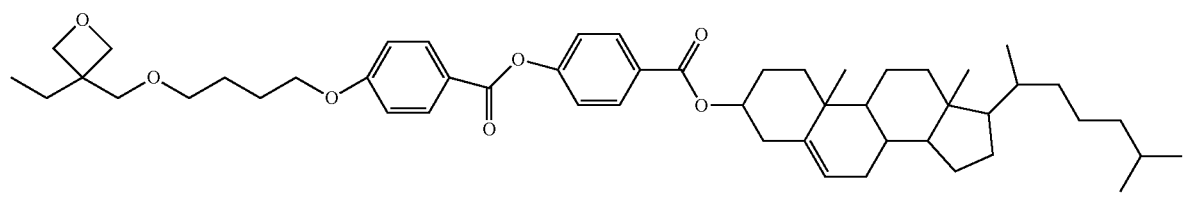
(1-107)
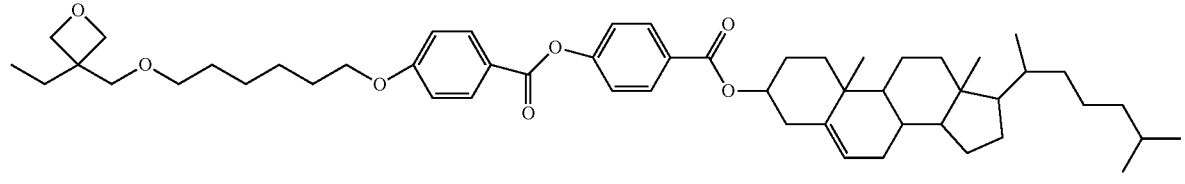
(1-108)
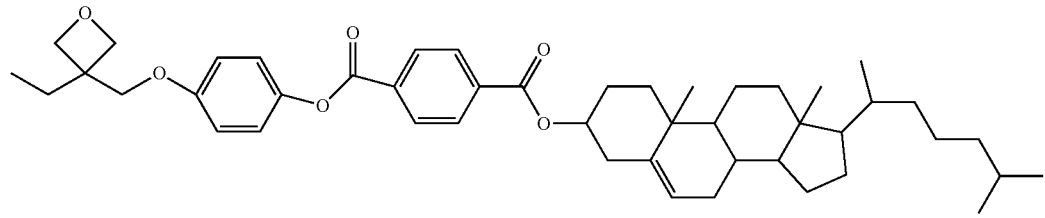
(1-109)

(1-110)
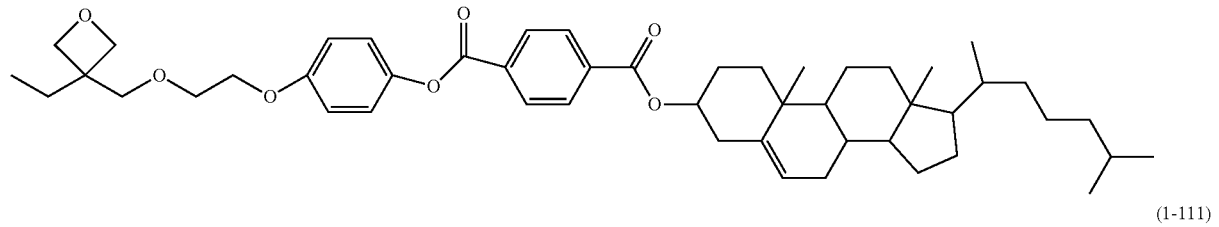
(1-111)
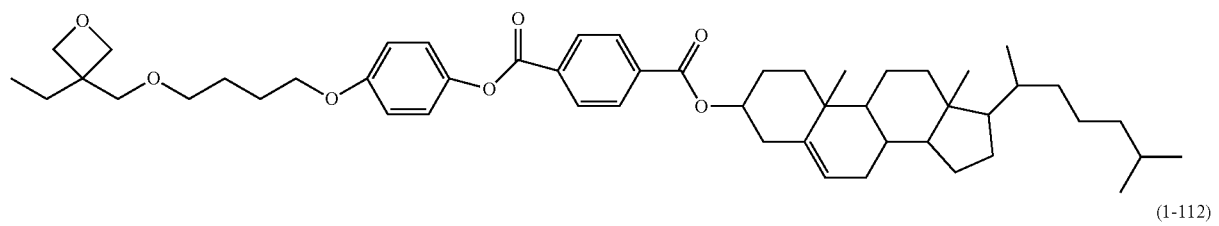
(1-112)
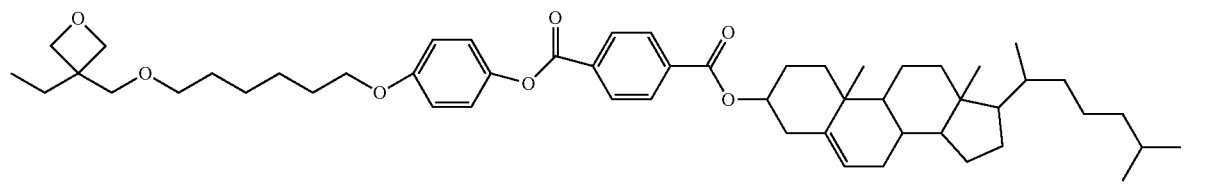
(1-113)
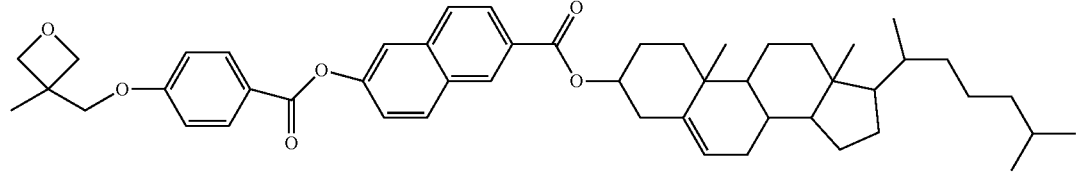
(1-114)
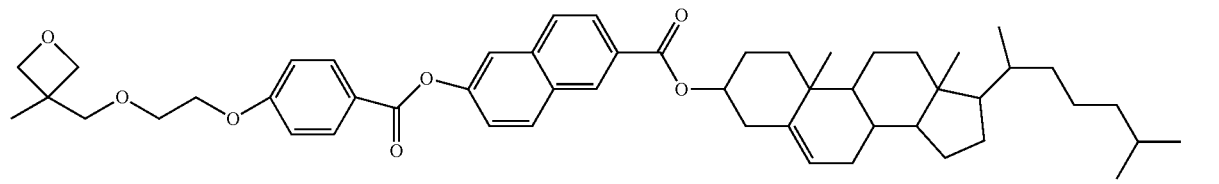
(1-115)
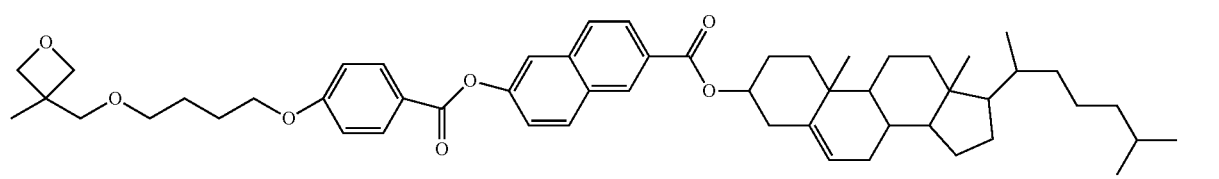
(1-116)
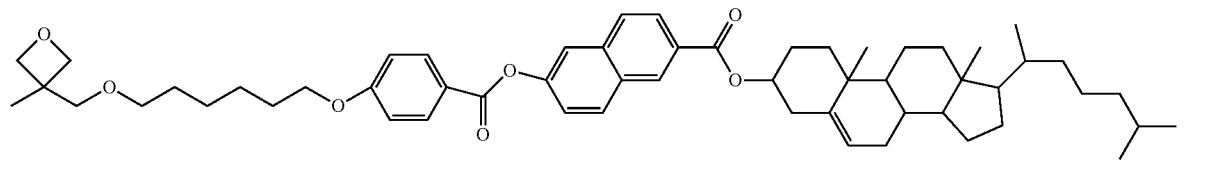
(1-117)
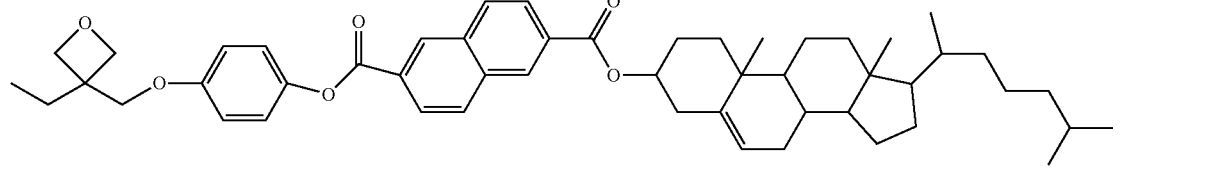

(1-118)
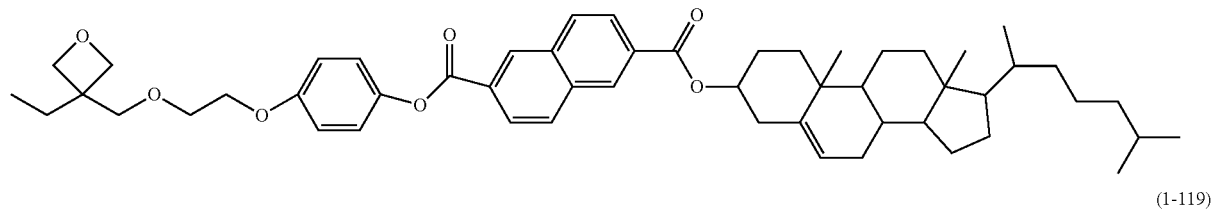
(1-119)
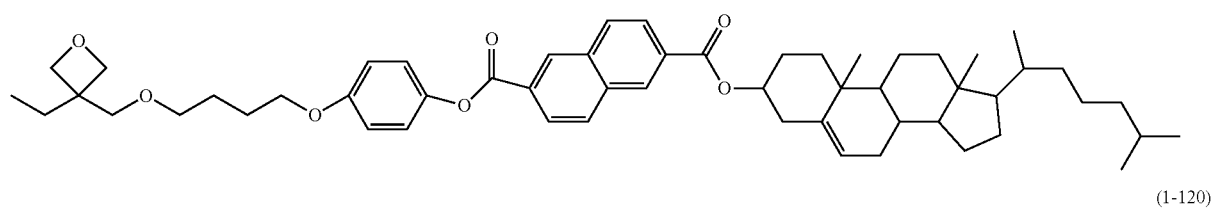
(1-120)
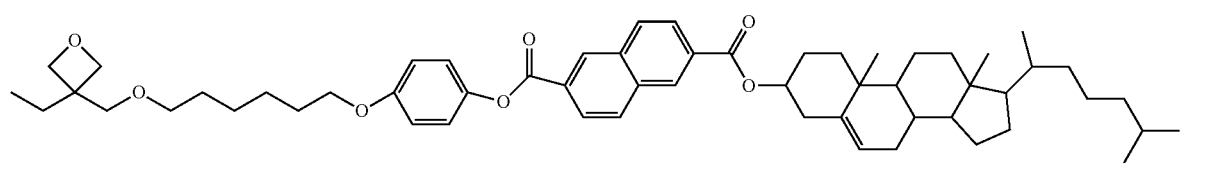
(1-121)
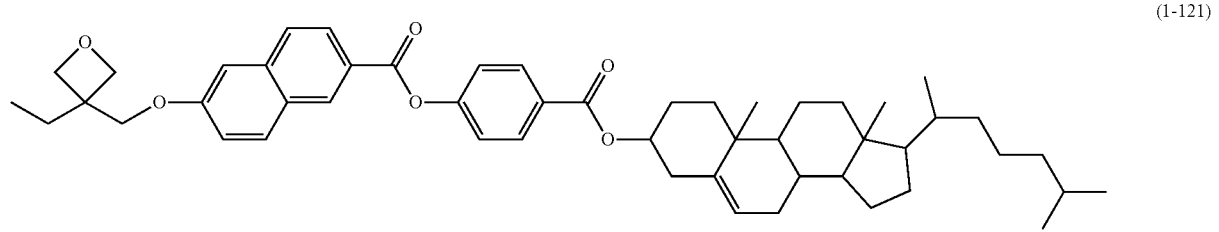
(1-122)
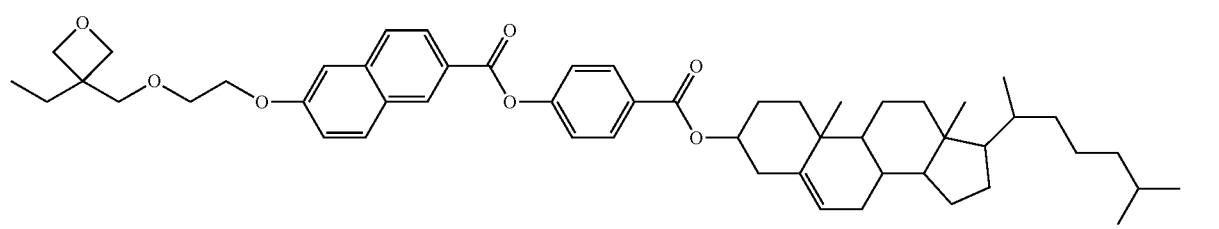
(1-123)
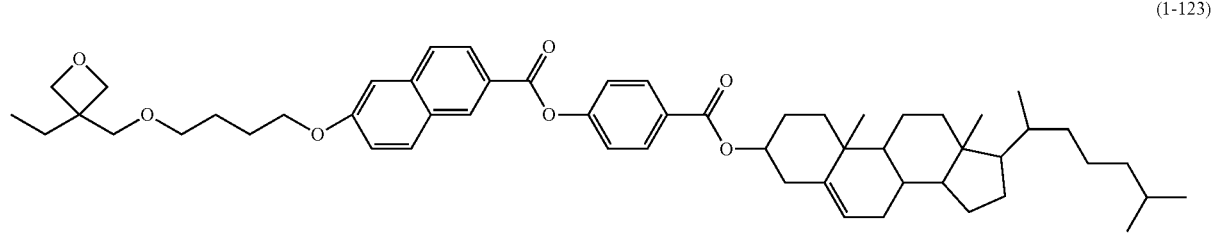
(1-124)
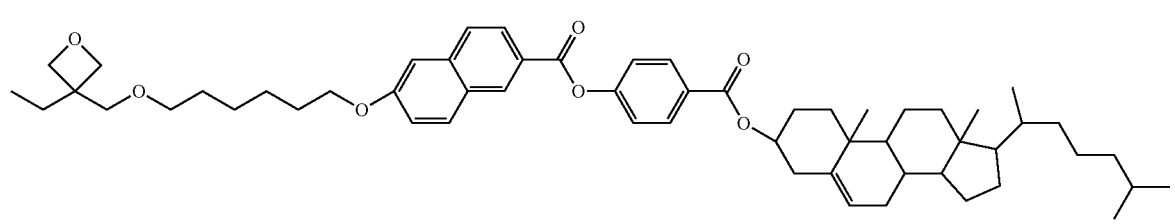

(1-125)
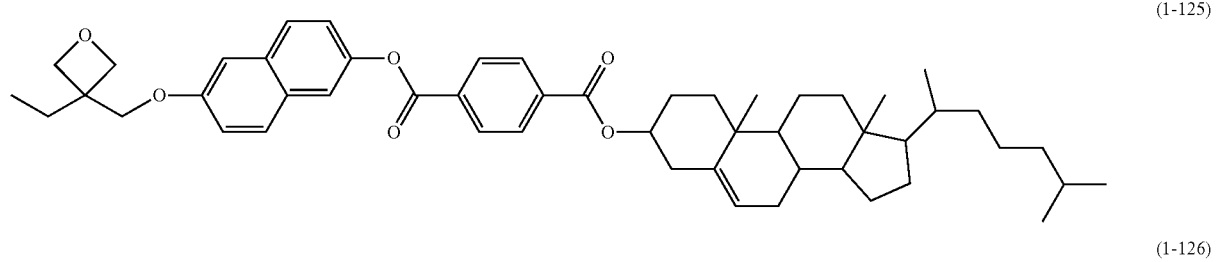
(1-126)
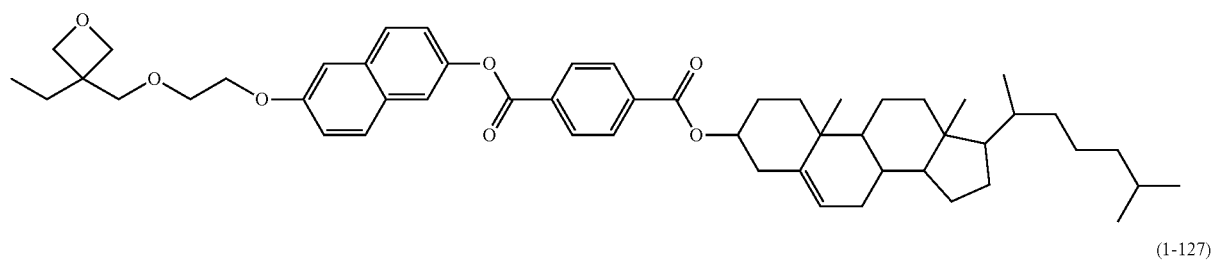
(1-127)
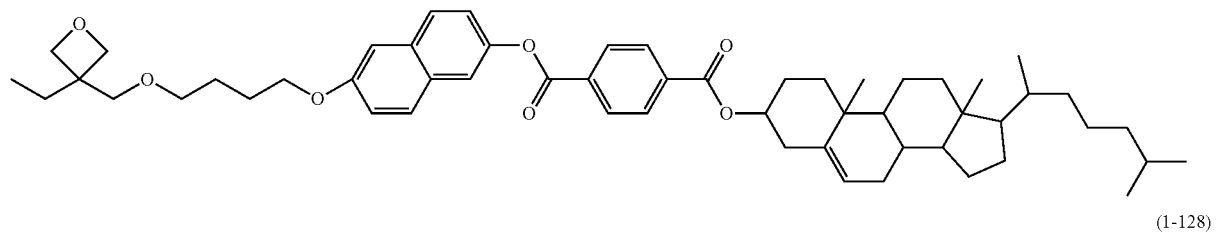
(1-128)
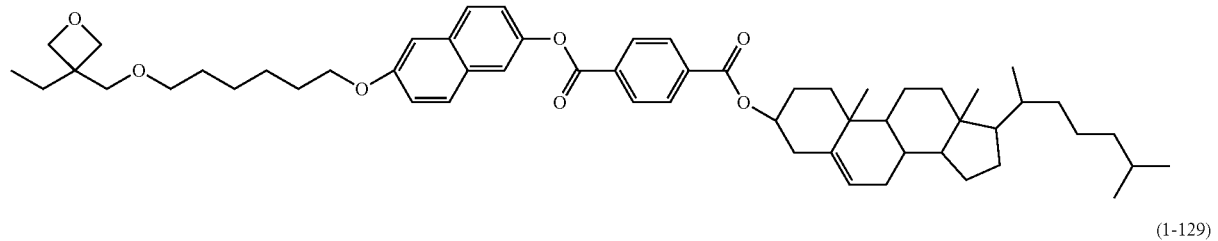
(1-129)
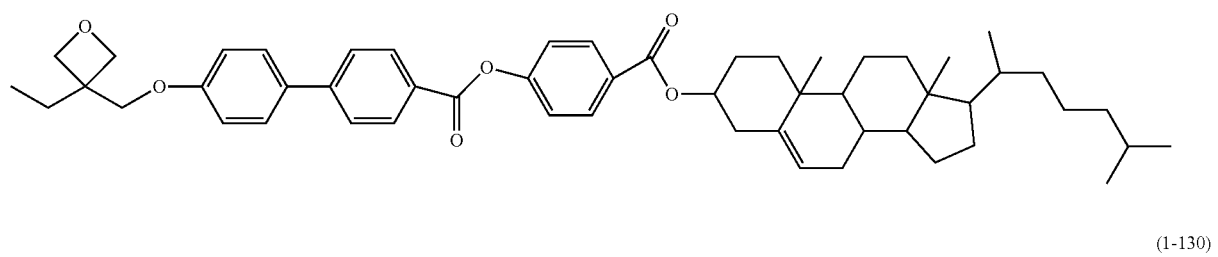
(1-130)
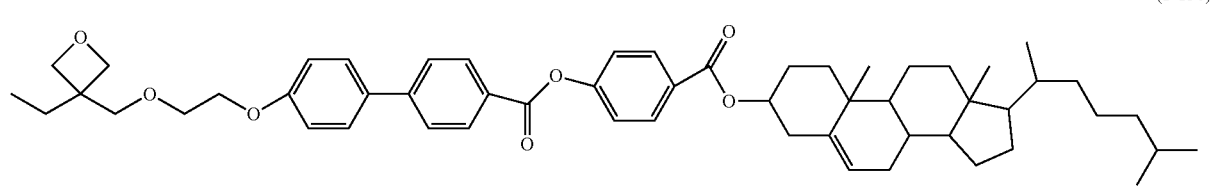
(1-131)
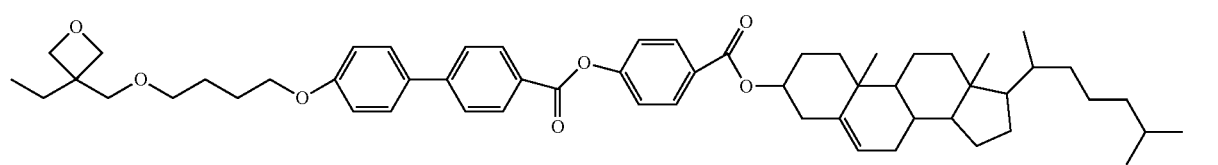

-continued
(1-132)
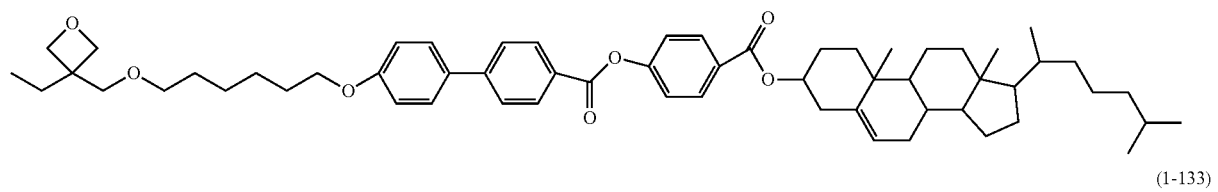
(1-133)
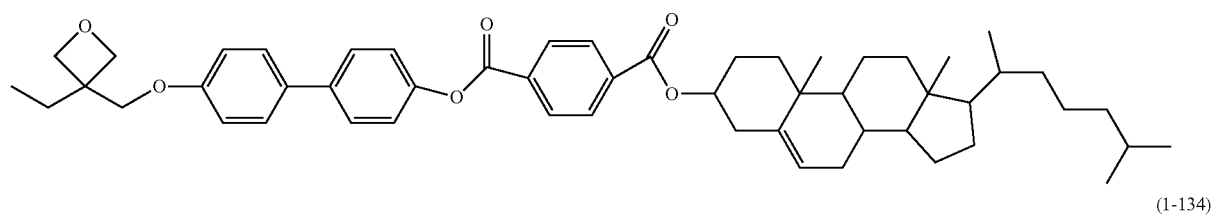
(1-134)
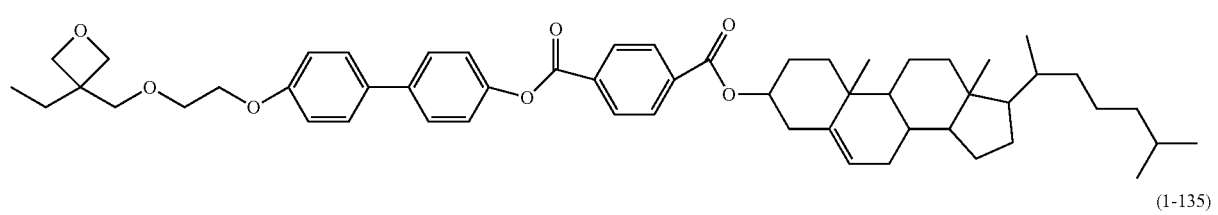
(1-135)
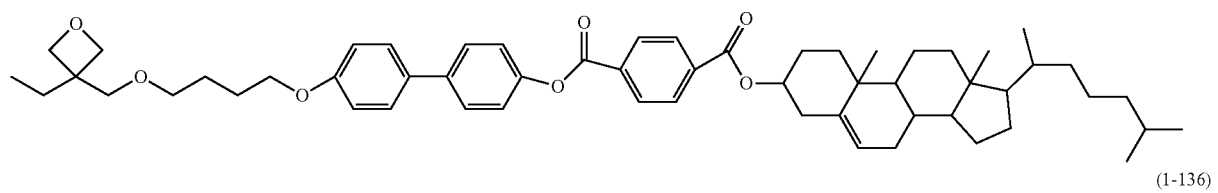
(1-136)
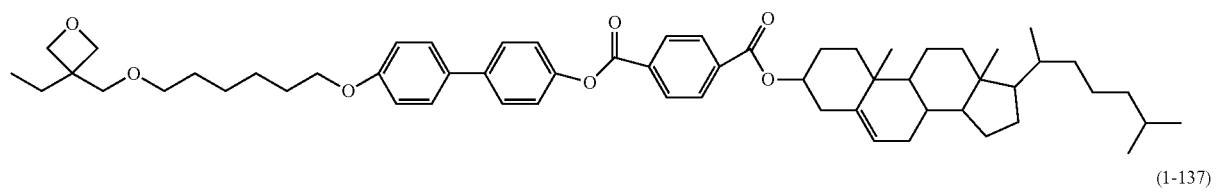
(1-137)
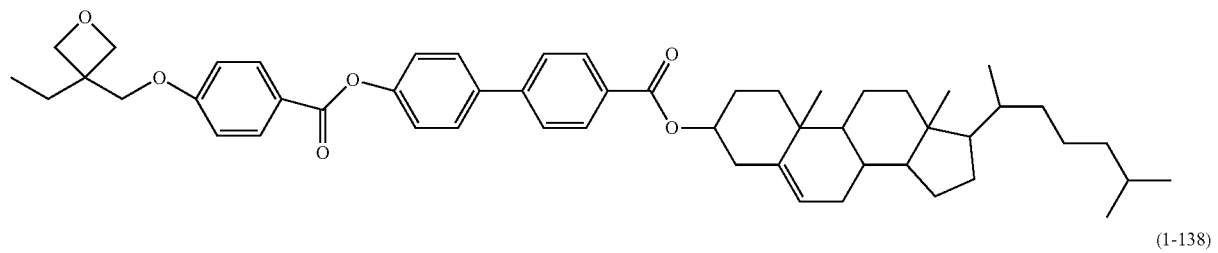
(1-138)
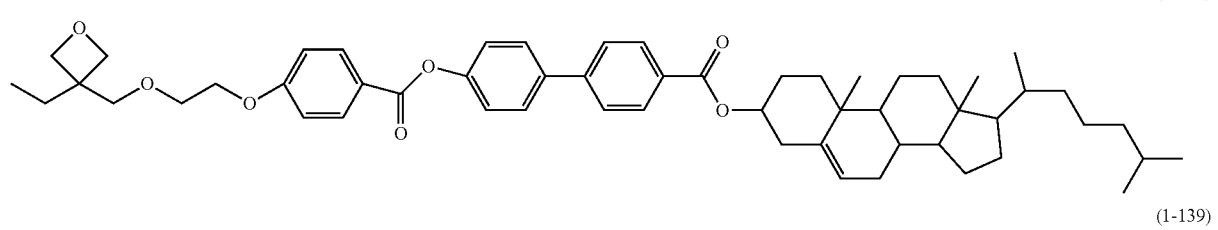
(1-139)
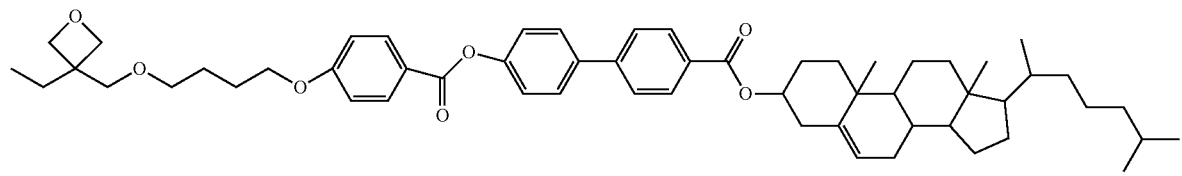

(1-140)
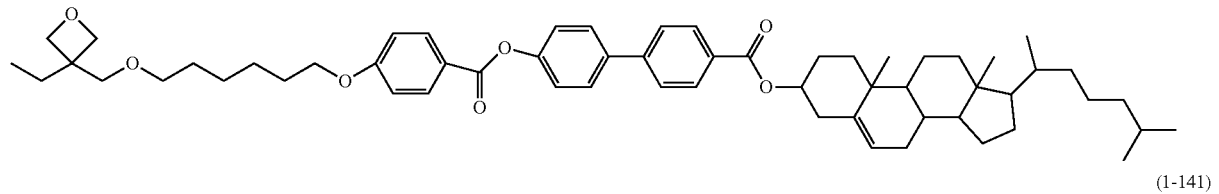
(1-141)
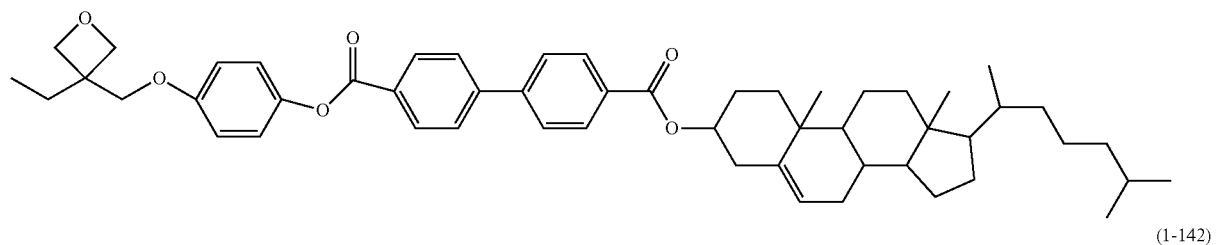
(1-142)
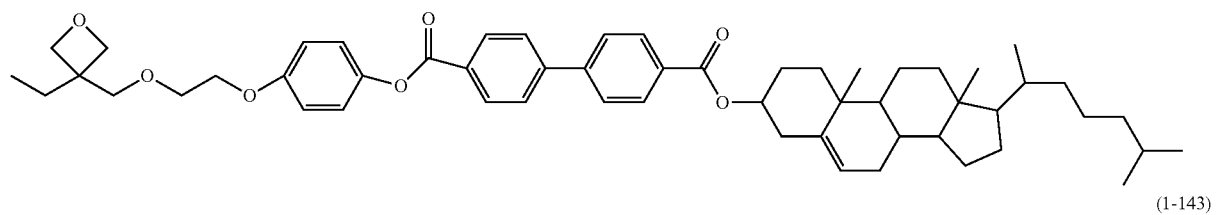
(1-143)
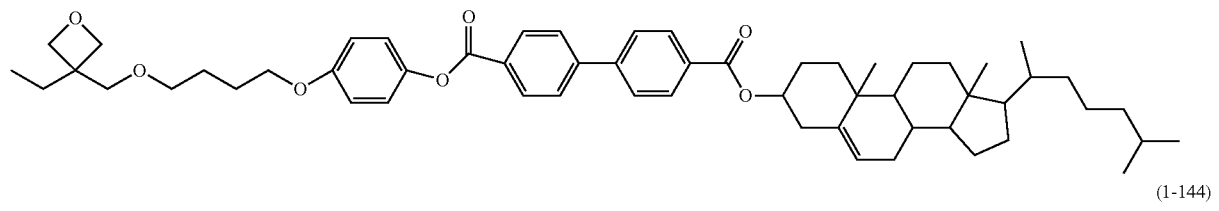
(1-144)
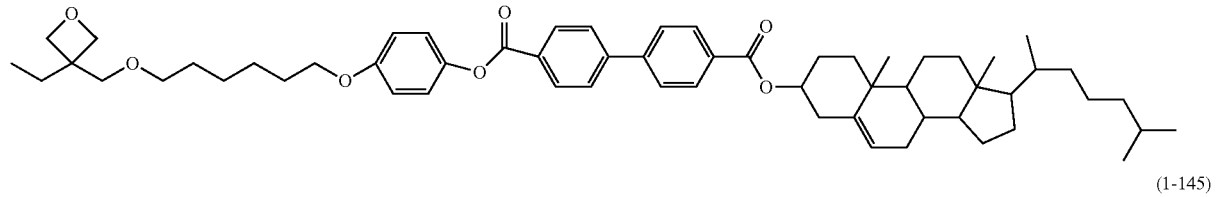
(1-145)
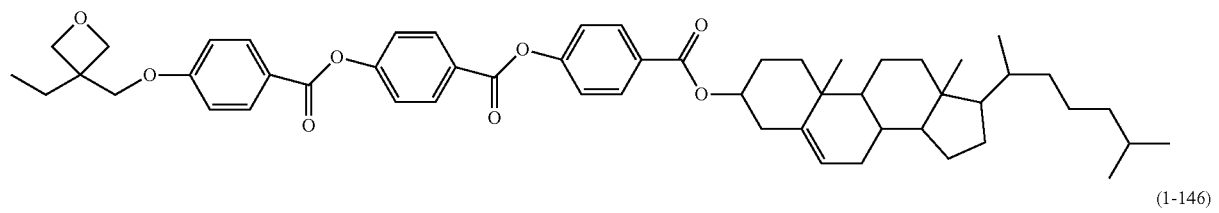
(1-146)
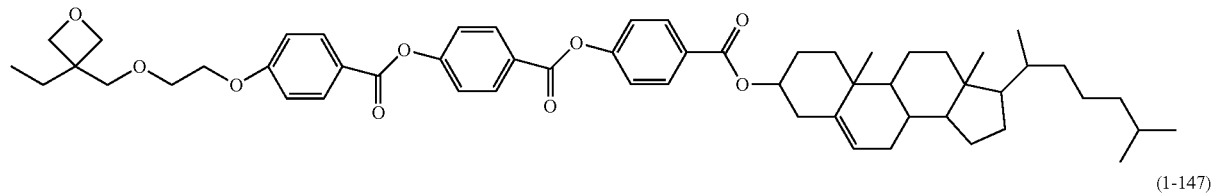
(1-147)
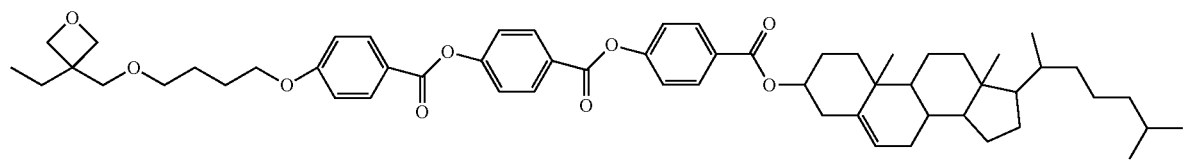

-continued
(1-148)
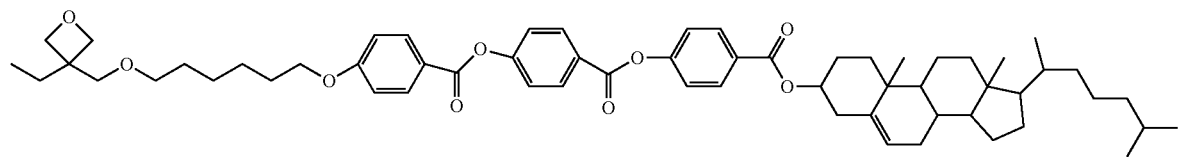
(1-149)
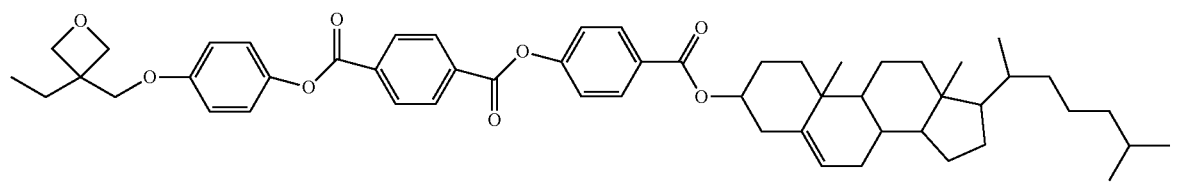
(1-150)
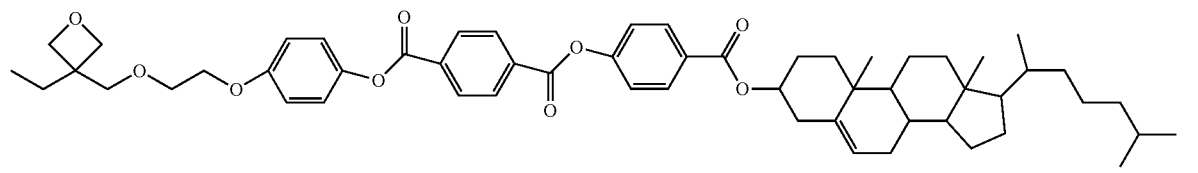
(1-151)
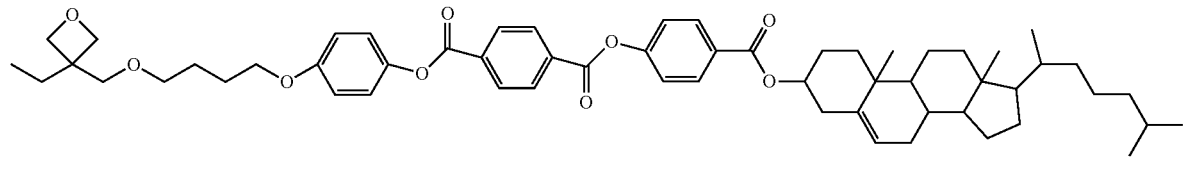
(1-152)
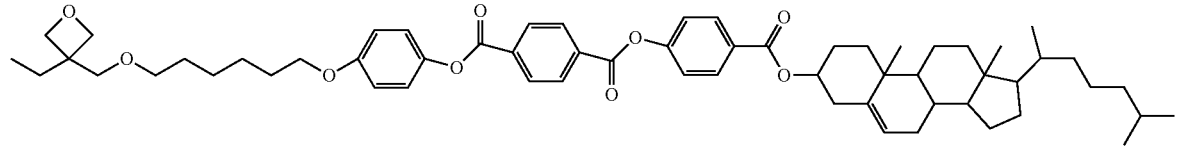
(1-153)
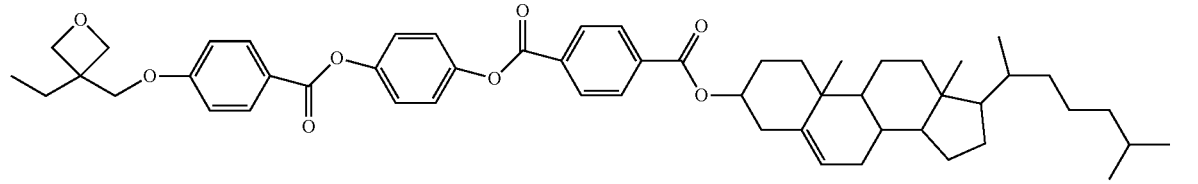
(1-154)
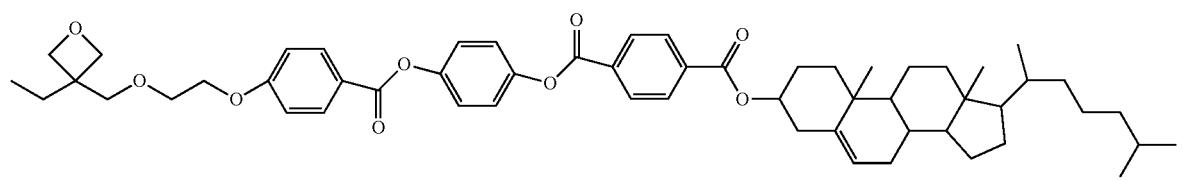
(1-155)
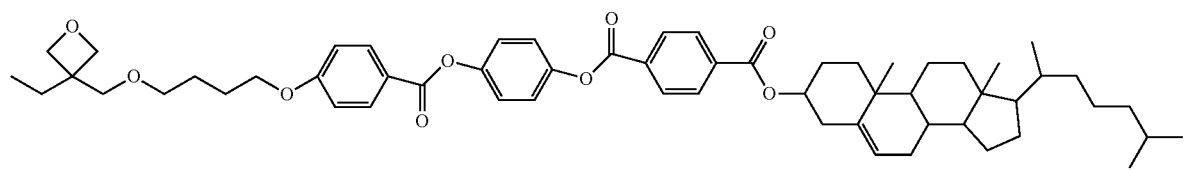

(1-156)
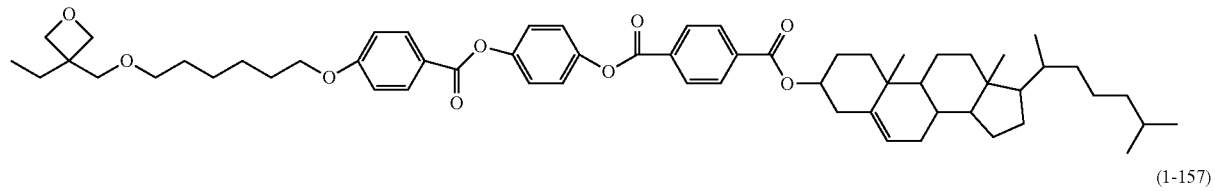

(1-157)
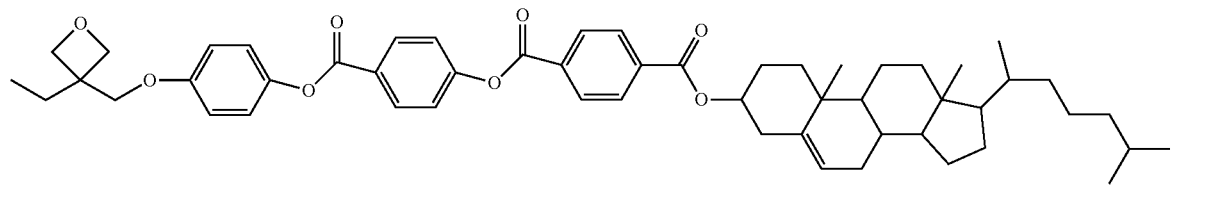

(1-158)
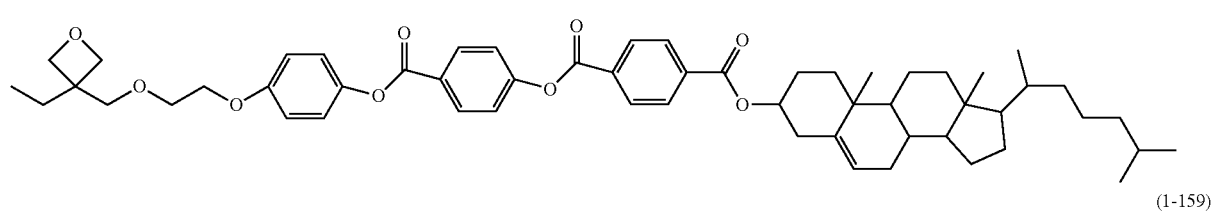

(1-159)
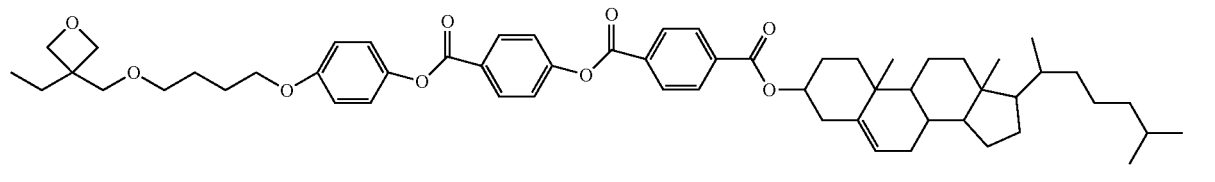

(1-160)

[Liquid Crystal Compositions]

The liquid crystal composition of the invention includes the compound (1) and a liquid crystal compound. In the present invention, the compound (1) may be used alone or two or more of the compound (1) may be used. Similarly, the liquid crystal compounds may be used alone or two or more of the liquid crystal compounds may be used. The liquid crystal compound may be a non-polymerizable compound or polymerizable compound. It is desirable that at least one of the liquid crystal compounds is a polymerizable compound.

Examples of the non-polymerizable liquid crystal compound are described in LiqCryst (LCI Publisher GmbH, Hamburg, Germany) that is a database of liquid crystal compounds. Examples of the polymerizable liquid crystal compound include the compounds represented by the following formulas (M1a), (M1b), (M1c), (M2a), (M2b), (M2c), and the like.

(M1a)
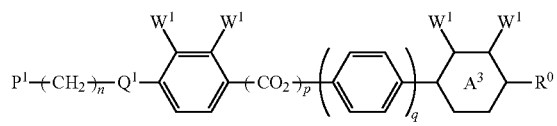

(M1b)
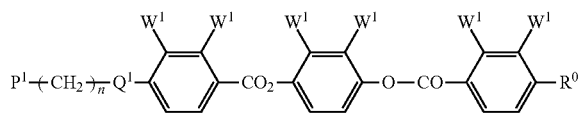

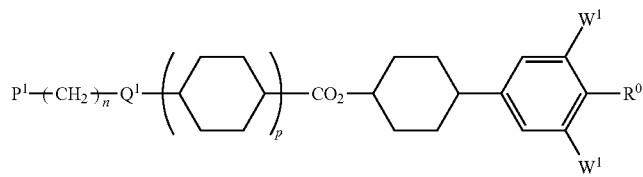
(M1c)

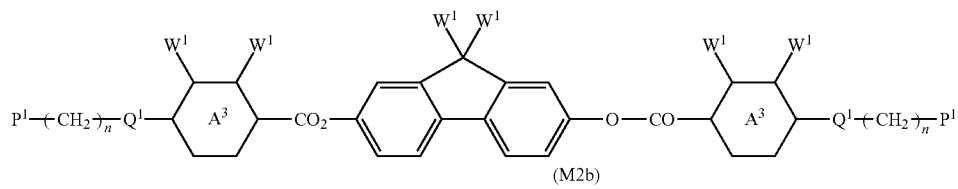
(M2a)

(M2b)  (M2c)

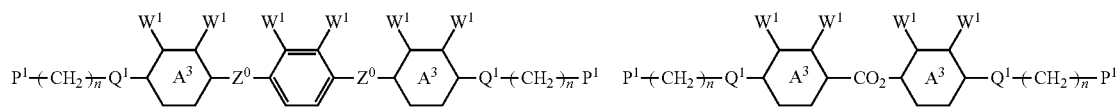

In formulas (M1a) to (M2c), P¹ is independently a monovalent group represented by any one of the following formulas (P1) to (P8); R⁰ is independently hydrogen, fluorine, chlorine, —CN or alkyl having 1 to 20 carbons, and in the alkyl, arbitrary —CH₂— may be replaced by —O—, —COO— or —OCO—, and arbitrary hydrogen may be replaced by halogen; the ring A³ is independently 1,4-cyclohexylene or 1,4-phenylene; W¹ is independently hydrogen, halogen, alkyl having 1 to 3 carbons or halogenated alkyl having 1 to 3 carbons; Q¹ is independently a single bond or alkylene having 1 to 20 carbons, and in the alkylene, arbitrary —CH₂— may be replaced by —O—, —COO— or —OCO—; Z⁰ is independently —COO—, —OCO—, —CH₂CH₂—, —CH₂O—, —OCH₂—, —CH₂CH₂COO—, —OCOCH₂CH₂—, —CH=CHCOO— or —OCOCH=CH—; p and q are each independently 0 or 1, and n is an integer from 0 to 10.

In formulas (M1a) to (M2c), when one compound has a plurality of P¹, arbitrary two P¹ may be the same substituents or different substituents. The same rule applies to Q¹, Z⁰, A³ and W¹.

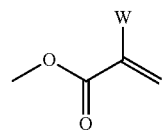
(P1)

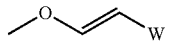
(P2)

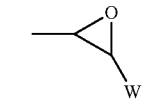
(P3)

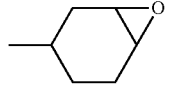
(P4)

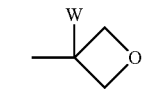
(P5)

-continued

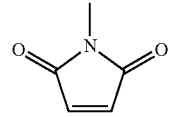
(P6)

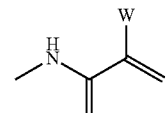
(P7)

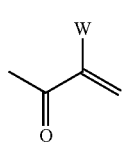
(P8)

In formulas (P1) to (P8), W is hydrogen, halogen, alkyl having 1 to 3 carbons or halogenated alkyl having 1 to 3 carbons.

The liquid crystal composition of the invention has a wide temperature range of a cholesteric phase at around room temperature (at about 10° C. to about 40° C.). A wavelength range of light, which the cholesteric phase reflects, can be adjusted by varying the component ratio of the composition or polymerization temperature of the composition. This adjustment makes it possible to form a polymer that reflects light having a desired color or a wavelength for a purpose. The compound (1) is a chiral agent which has an excellent compatibility, a large HTP, and a small temperature dependency of the HTP. The liquid crystal composition of the invention includes the chiral agent and a liquid crystal compound, and thus an adjustment of the temperature range of a cholesteric phase or of the wavelength range of selective reflection is especially easy.

In the liquid crystal composition of the invention, the content of the compound (1) is preferably in the range of 0.05 to 40% by weight, more preferably in the range of 0.5 to 35% by weight, still more preferably in the range of 1.0 to 30% by weight based on the total amount (100% by weight) of the compound (1) and the liquid crystal compound. A cholesteric liquid crystal material that has the wavelength range of selective reflection and its polymer can be obtained when the content of the compound (1) falls in these ranges.

The liquid crystal composition of the invention may further include, for example, a non-liquid crystal polymerizable compound, solvent, a polymerization initiator, surfactant, an ultraviolet light absorbent, filler, a sensitizer, and so forth in addition to the compound (1) and the liquid crystal compound in such an amount that does not reduce the advantages of the invention. Any optically active compound other than the compound (1) may be added to the liquid crystal composition of the invention in order to optimize the characteristics of the polymer.

[Polymers]

The polymer of the invention can be formed by polymerization of the liquid crystal composition of the invention described above. A cholesteric phase (a helical structure) of the composition is fixed by means of polymerization, and thus the polymer reflects light having a desired color or having a desired wavelength which is in accordance with a purpose. The polymerization of the composition may be thermal polymerization by means of heating, photopolymerization by irradiation with light, or their combinations.

A desirable kind of light used for the photopolymerization is ultraviolet light, visible light, infrared light and so forth, and electron beams or electromagnetic waves such as X-rays may also be used. The ultraviolet light or visible light is usually used. The wavelengths are preferably in the range of 150 to 500 nm, more preferably in the range of 250 to 450 nm, and most preferably in the range of 300 to 400 nm. Examples of a light source include a low pressure mercury lamp (a germicidal lamp, a chemical fluorescent lamp and a black light), a high pressure discharge lamp (a high pressure mercury lamp and a metal halide lamp) and a short-arc discharge lamp (an ultra high-pressure mercury lamp, a xenon lamp and a mercury-xenon lamp), and the high pressure mercury lamp is desirable.

The composition may be irradiated with light directly from a light source, or light with a specific wavelength (or a specific wavelength range) selected by use of an optical filter. The irradiation energy density is preferably in the range of 2 to 5000 mJ/cm$^2$, more preferably in the range of 10 to 3000 mJ/cm$^2$, and most preferably in the range of 100 to 2000 mJ/cm$^2$. The irradiance is preferably in the range of 0.1 to 5000 mW/cm$^2$, and more preferably in the range of 1 to 2000 mW/cm$^2$.

The shape of the polymer is not specially limited, and it may be a film-shaped (the form of a film), a plate-shaped and so forth, and the polymer may also be molded in various shape. The film can be formed by applying the liquid crystal composition of the invention to a substrate, and then polymerizing the composition.

The compound (1) has an excellent compatibility, a large HTP and a small temperature dependency of the HTP. The polymer of the invention is formed by polymerization of the liquid crystal composition including the compound (1) and a liquid crystal compound, selectively reflects light with the wavelength for a purpose (near infrared way, visible light, near ultraviolet radiation, and the like) and is transparent. Thus, such a polymer can suitably be used for a display device, a reflective sheet (a reflective film) such as a solar radiation heat reflective sheet, or a pigment.

[Use]

The use of the liquid crystal composition and the polymer of the invention include cosmetics, anti-counterfeit printed matters, ornaments optical films, and the like. The composition and the polymer can also be used for general color materials such as liquid crystal pigments, coating materials, spraying inks and printing inks.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

Hereafter, the invention will be explained in more detail on the basis of examples. However, the scope of the invention should not be limited to these examples.

Synthetic Example 1

The compound (D) below was synthesized by the following method (the first step to the sixth step).

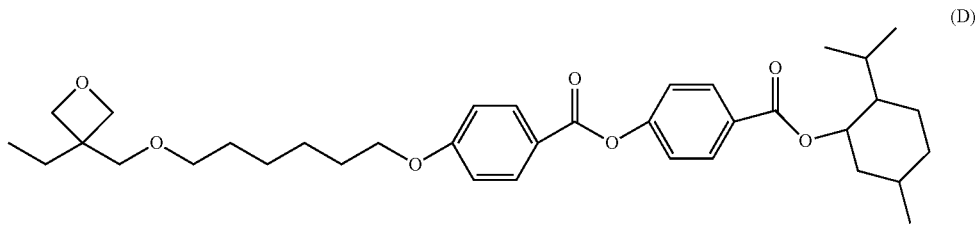 [SMILES: CCC1(COCCCCCCOc2ccc(C(=O)Oc3ccc(C(=O)OC4CC(C)CCC4C(C)C)cc3)cc2)COC1]

The first step:

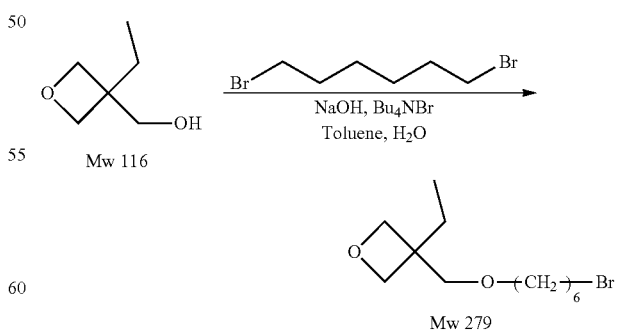

Toluene (2.5 L), 3-ethyl-3-oxetanemethanol (500 g) and 1,6-dibromohexane (1500 g) were sequentially added with stirring to sodium hydroxide (860 g) dissolved in water (2 L). Tetrabutylammonium bromide (161 g) dissolved in water (500 ml) was added dropwise to the mixture, and the mixture was refluxed for 4 hours. After the reaction, the water phase was separated. The toluene phase was washed with brine, and the solvent was distilled off under reduced pressure. The residue was purified by distillation under reduced pressure, giving the objective ether (480 g) in 40% yield.

The Second Step:

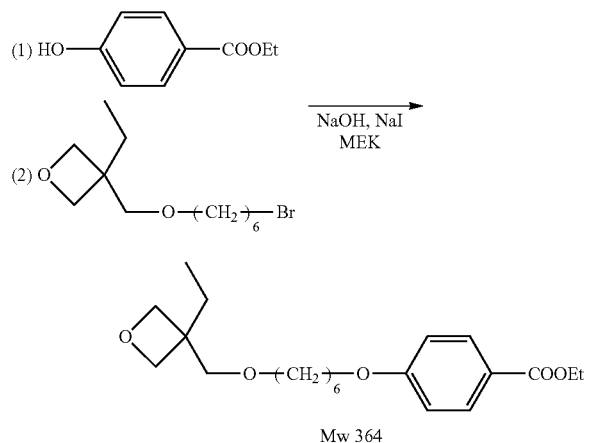

A mixture of 2-butanone (3 L), ethyl 4-hydroxybenzoate (500 g) and sodium hydroxide (144 g) was stirred at a temperature range of 30° C. to 40° C. Sodium iodide (536 g) and 3-[(6-bromohexyloxy)methyl]-3-ethyloxetane (1000 g) were added to the mixture, and the mixture was refluxed. After the reaction, the reaction mixture was filtered, the filtrate was washed with water and brine and the organic solvent was distilled off under reduced pressure. The residue was purified by distillation under reduced pressure, giving the objective ester (737 g) in 67% yield.

The third step:

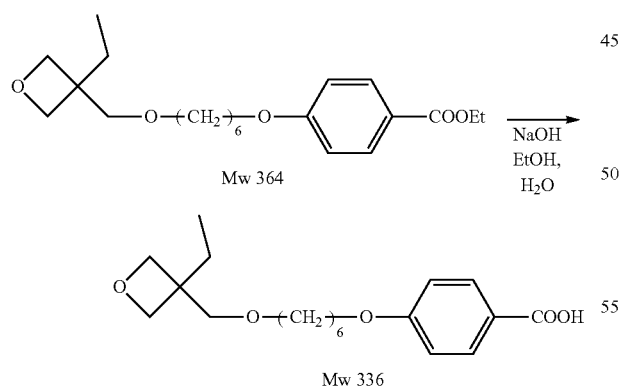

Ethanol (1 L) and then the ester (514 g) formed in the second step were added to sodium hydroxide (112 g) dissolved in water (1 L), and the mixture was refluxed. After the reaction, ethanol was distilled off under reduced pressure. Dilute hydrochloric acid was added to the residue, and solids deposited were washed with water, giving the objective carboxylic acid (461 g) in 97% yield.

The forth step:

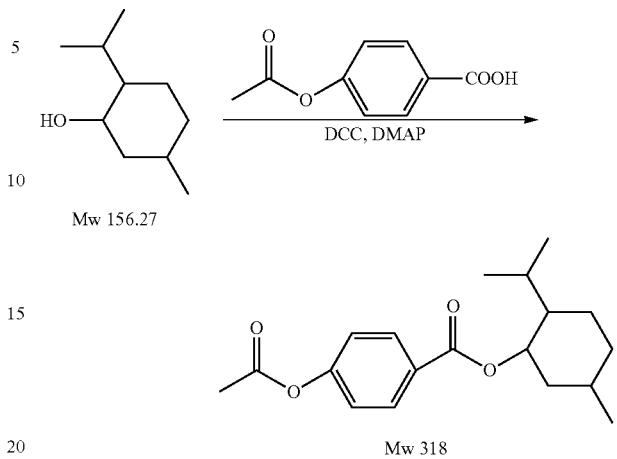

A mixture of 4-acetoxybenzoic acid (3.6 g), L-menthol (3.2 g), dicyclohexylcarbodiimide (DCC; 5.0 g), N,N-dimethyl-4-aminopyridine (DMAP; 0.24 g) and dichloromethane (50 mL) was stirred at room temperature for 1 hour. Crystals deposited were filtered off, water (50 mL) was added to the filtrate, and a dichloromethane solution was separated. The dichloromethane solution was washed well sequentially with a dilute hydrochloric acid, a saturated aqueous solution of sodium hydrogencarbonate and water, dried over anhydrous magnesium sulfate and the solvent was distilled off under reduced pressure, and the residue was purified by means of column chromatography (silica gel; eluent: toluene/ethyl acetate=50/1 by volume), giving yellow brown solids (4.2 g).

The fifth step:

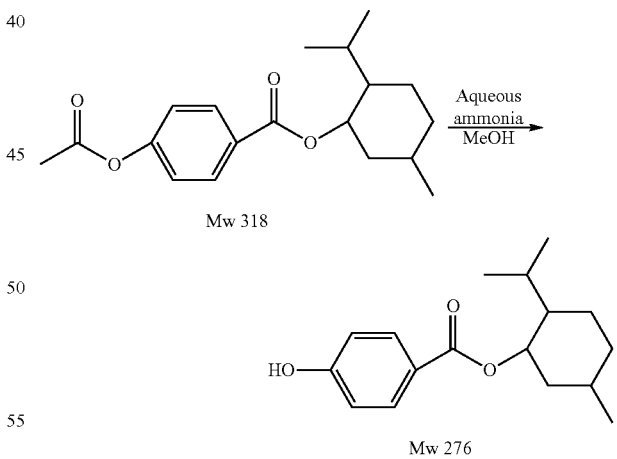

Methanol (20 mL) was added to the solid (4.2 g) formed in the fourth step, and a 30%-aqueous solution of ammonia (2 mL) was added thereto dropwise at room temperature. After the mixture had been stirred at room temperature for 2 hours, 6N-hydrochloric acid (30 mL) was added to the reaction mixture for neutralization. The mixture was extracted with ethyl acetate (200 mL) and the extract was dried over anhydrous magnesium sulfate. The solvent was distilled off under reduced pressure from the extraction liquid, giving a residue.

The Sixth Step:

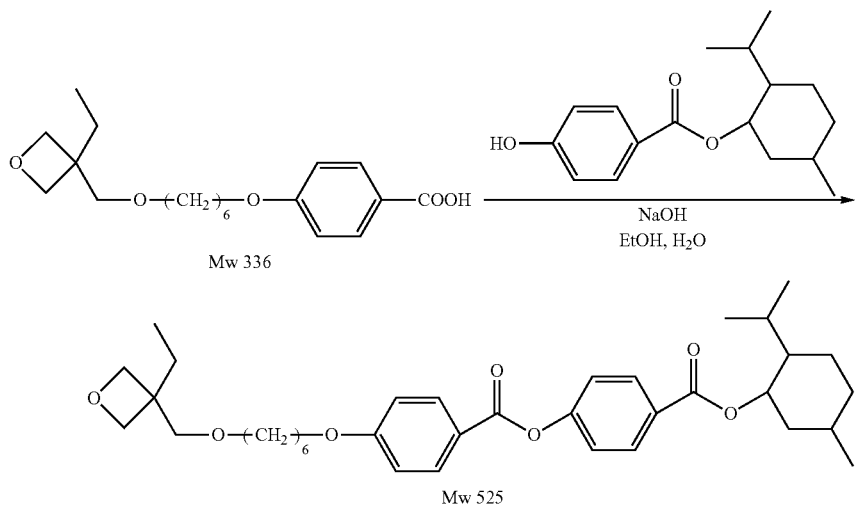

A mixture of the residue (3.1 g) formed in the fifth step, the carboxylic acid (3.6 g) formed in the third step, DCC (2.7 g), DMAP (0.14 g) and dichloromethane (100 mL) was stirred at room temperature for 1 hour. Crystals deposited were filtered off, water (50 mL) was added to the filtrate, and the dichloromethane solution was separated. The dichloromethane solution was washed well sequentially with a dilute hydrochloric acid, a saturated aqueous solution of sodium hydrogencarbonate and water, and then dried over anhydrous magnesium sulfate. The solvent was distilled off under reduced pressure, and the residue was purified by means of column chromatography (silica gel; eluent: toluene/ethyl acetate=50/1 by volume), giving a transparent oil (3.7 g). Results of the NMR analysis of the obtained compound are as described below.

$^1$H-NMR (CDCl$_3$; δ ppm): 0.81-2.17 (m, 31H), 3.48 (t, 2H), 3.53 (s, 2H), 4.05 (t, 2H), 4.38 (d, 2H), 4.45 (d, 2H), 4.90 (m, 1H), 6.97 (d, 2H), 7.27 (d, 2H), 8.11 (d, 2H) and 8.14 (d, 2H).

It was confirmed from the NMR analysis that the compound obtained finally in Synthetic Example 1 had the structure (D) described above.

Synthetic Example 2

The compound (E) below was synthesized by the following method (the first step to the third step).

The First Step:

A mixture of the residue (5.0 g) formed in the fifth step of Synthetic Example 1, 4-acetoxybenzoic acid (3.1 g), DCC (4.4 g), DMAP (0.2 g) and dichloromethane (100 mL) was stirred at room temperature for 1 hour. Crystals deposited were filtered off, and water (50 mL) was added to the filtrate, and a dichloromethane solution was separated. The dichloromethane solution was washed well sequentially with dilute hydrochloric acid, a saturated aqueous solution of sodium hydrogencarbonate and water, and dried over anhydrous magnesium sulfate. The solvent was distilled off under reduced pressure from the solution, and the residue was purified by means of column chromatography (silica gel; eluent: toluene/ethyl acetate=10/1 by volume), giving yellow brown solids (5.5 g).

The Second Step:

Methanol (20 mL) was added to the solid (5.5 g) formed in the first step, and a 30%-aqueous solution of ammonia (2 mL) was added thereto dropwise at room temperature. After the mixture had been stirred for 2 hours, 6N-hydrochloric acid (30 mL) was added to the reaction mixture for neutralization. The mixture was extracted with ethyl acetate (200 mL) and the extraction liquid was dried over anhydrous magnesium sulfate. The solvent was distilled off under reduced pressure from the extraction liquid, giving a residue.

The Third Step:

A mixture of the residue (4.0 g) formed in the second step, the carboxylic acid (3.2 g) formed in the third step of Synthetic Example 1, DCC (2.7 g), DMAP (0.1 g) and dichlo- (E)

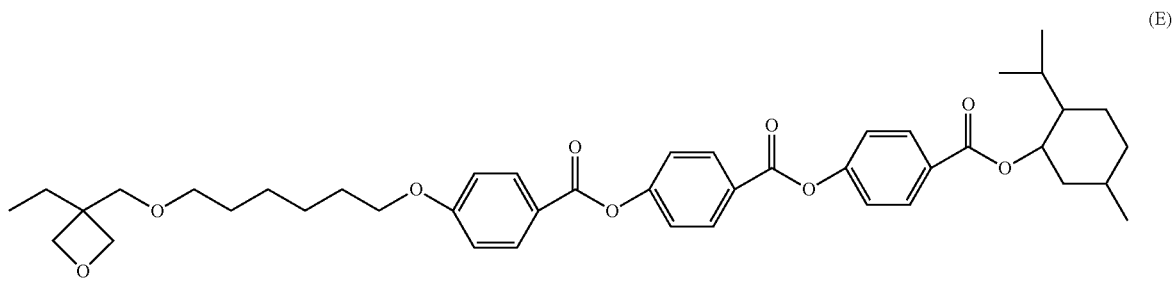 [SMILES: CCC1(COCCCCCCOc2ccc(C(=O)Oc3ccc(C(=O)Oc4ccc(C(=O)OC5CC(C)CCC5C(C)C)cc4)cc3)cc2)COC1]

romethane (100 mL) was stirred at room temperature for 1 hour. Crystals deposited was filtered off, and water (50 mL) was added to the filtrate, and a dichloromethane solution was separated. The dichloromethane solution was washed well sequentially with a dilute hydrochloric acid, a saturated aqueous solution of sodium hydrogencarbonate and water, and dried over anhydrous magnesium sulfate. The solvent was distilled off under reduced pressure from the solution, and the residue was purified by means of column chromatography (silica gel; eluent: toluene/ethyl acetate=50/1 by volume), giving a transparent oil (3.3 g). Results of the NMR analysis of the obtained compound are as described below.

$^1$H-NMR (CDCl$_3$; δ ppm: 0.81-2.17 (m, 31H), 3.48 (t, 2H), 3.53 (s, 2H), 4.05 (t, 2H), 4.38 (d, 2H), 4.45 (d, 2H), 4.90 (m, 1H), 6.98 (m, 2H), 7.26-7.39 (m, 4H) and 8.12-8.30 (m, 6H).

It was confirmed from the NMR analysis that the compound obtained finally in Synthetic Example 2 had the structure (E) described above.

Synthetic Example 3

The compound (F) below was synthesized by the following method (one step).

pressure from the solution, and the residue was purified by means of column chromatography (silica gel; eluent: toluene/ethyl acetate=10/1 by volume), giving yellow brown solids (9.0 g). Results of the NMR analysis of the obtained compound are as described below.

$^1$H-NMR (CDCl$_3$; δ ppm): 0.68-2.10 (m, 54H), 3.47 (t, 2H), 3.52 (s, 2H), 4.02 (t, 2H), 4.38 (d, 2H), 4.45 (d, 2H), 4.82 (m, 1H), 5.40 (s, 1H), 6.88 (d, 2H) and 7.98 (d, 2H).

It was confirmed from the NMR analysis that the compound obtained finally in Synthetic Example 3 had the structure (F) described above.

<Selective Reflection Film>

(1) Orientation Treatment for a Supporting Substrate

A PET film (Lumirror T60, Toray Industries, Inc.) with a thickness of 50 micrometers was used as a supporting substrate. A rubbing treatment was carried out with a rayon cloth.

(2) Polymerization Conditions

The PET film to which a liquid crystal composition was applied was irradiated with light at an irradiance of 30 mW/cm$^2$ (365 nm) in air at room temperature for 30 seconds by use of a 250 W ultra-high pressure mercury lamp, giving a cured film.

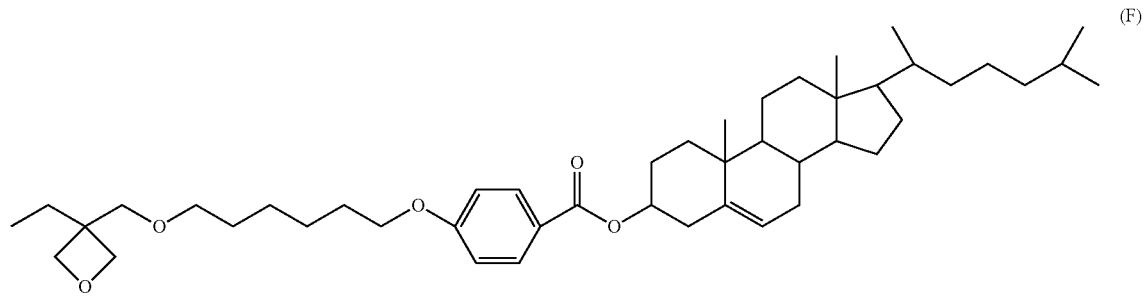 [SMILES: CCC1(COCCCCCCOc2ccc(C(=O)OC3CCC4(C)C(=CCC5C4CCC4(C)C(C(C)CCCC(C)C)CCC54)C3)cc2)COC1]

(F)

A mixture of the carboxylic acid (6.4 g) formed in the third step of Synthetic Example 1, cholesterol (7.8 g), DCC (6.4 g), DMAP (0.3 g) and dichloromethane (200 mL) was stirred at room temperature for 1 hour. Crystals deposited were filtered off, water (50 mL) was added to the filtrate, and a dichloromethane solution was separated. The dichloromethane solution was washed well sequentially with a dilute hydrochloric acid, a saturated aqueous solution of sodium hydrogencarbonate and water, and then dried over anhydrous magnesium sulfate. The solvent was distilled off under reduced (3) Measurement of Selective Reflection Transmission spectrum of the cured film on the PET film was evaluated with ultraviolet-visible-near-infrared Spectrophotometer Model V-670 (JASCO Corporation). The selective reflection is indicated by the wavelength width of transmittance located in the middle of the maximum transmittance and the minimum transmittance. The central wavelength of selective reflection means the central value of the wavelength width.

Compounds used in the following Examples are listed below.

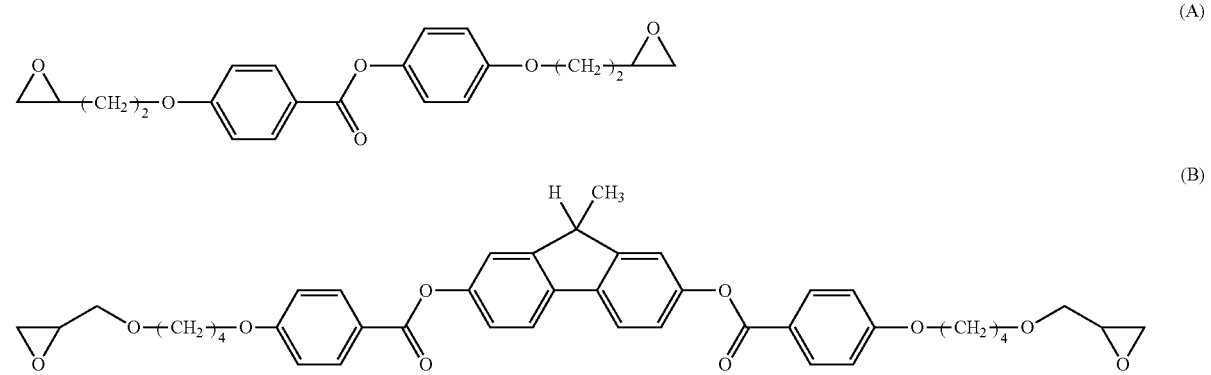

-continued

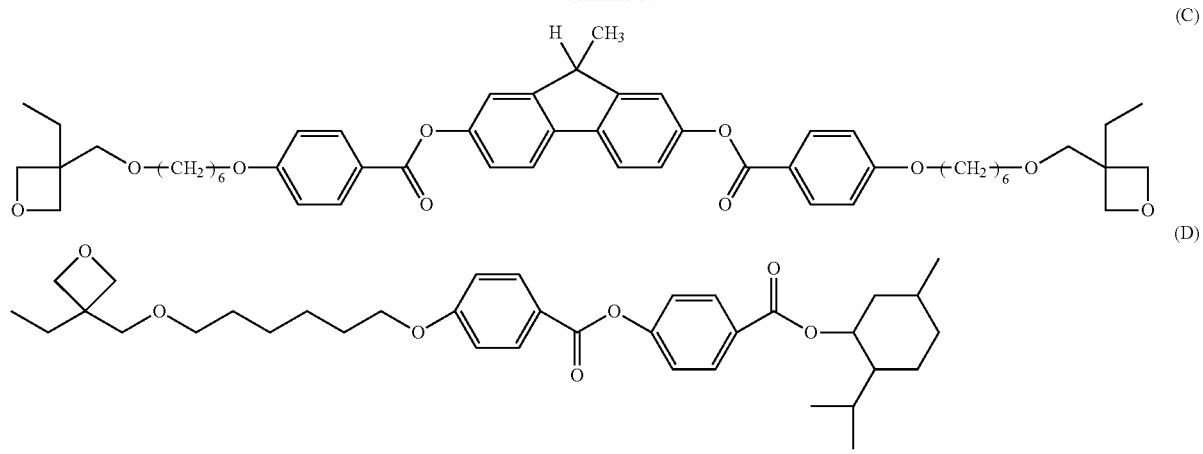

The compound (A) was synthesized according to the method described in Macromolecules, 26, 1244-1247 (1993). The compounds (B) and (C) were synthesized by the method described in JP 2005-060373 A. The compound (D) was synthesized by the method described in Synthetic Example 1 described above.

Example 1

Preparation of Polymerizable Liquid Crystal Compound (1)

The compounds are mixed in the weight ratio of the compound (A):the compound (B):the compound (C)=75:20:5. This composition is referred to as MIX (1). To 99.889 weight parts of the MIX (1), 0.10 weight part of the compound (D), 0.001 weight part of a fluorine based-nonionic surfactant FTX-218 (Neos Company Limited) and 0.01 weight part of a polymerization initiator CPI-110P (San-Apro Ltd.) were added, and cyclopentanone was further added thereto to give the polymerizable liquid crystal composition (1) having a solvent concentration of 30% by weight.

<Preparation of Selective Reflection Film>

The rubbing treated PET film was used as a supporting substrate. The polymerizable liquid crystal composition (1) was applied to the supporting substrate with a spin coater. The substrate was heated on a hot plate set up at 80° C. for 2 minutes for drying the solvent, allowing the liquid crystal phase to be oriented. The supporting substrate was irradiated with ultraviolet light (30 mW/cm², 365 nm) at 25° C. for 30 seconds by use of an ultra-high pressure mercury lamp (250 W), giving a liquid crystal film on the substrate. The film selectively reflected near infrared light, the central wavelength of selective reflection was 1000 nm, and the wavelength width was about 180 nm. The film was transparent and uniformly oriented.

Example 2

To 99.908 weight parts of the MIX (1), 0.08 weight part of the compound (D), 0.002 weight part of a fluorine based-nonionic surfactant FTX-218 (Neos Company Limited) and 0.01 weight part of a polymerization initiator CPI-110P (San-Apro Ltd.) were added, and cyclopentanone was further added thereto to give the polymerizable liquid crystal composition (2) having a solvent concentration of 30% by weight.

A liquid crystal film on the substrate was prepared in the same manner as that described in Example 1, except that the polymerizable liquid crystal composition (2) was used instead of the polymerizable liquid crystal composition (1). The film selectively reflected near infrared light, the central wavelength of selective reflection was 1200 nm, and the wavelength width was about 250 nm. The film was transparent and uniformly oriented.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A compound represented by the following formula (1):

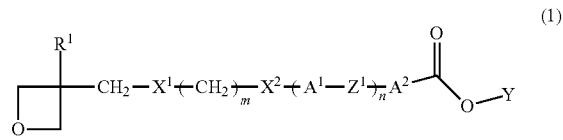

wherein $R^1$ is hydrogen, methyl or ethyl; $X^1$ is a single bond, —O— or —OCO—; $X^2$ is a single bond, —O—, —COO— or —OCO—; $A^1$ and $A^2$ are each independently a divalent aromatic ring or a divalent cyclohexane ring, and in these rings, arbitrary hydrogen may be replaced by halogen, alkyl having 1 to 3 carbons or halogenated alkyl having 1 to 3 carbons; $Z^1$ is independently a single bond, —O—, —S—, —COO—, —OCO—, —CH$_2$O—, —OCH$_2$—, —CH=CH—COO—, —OCO—CH=CH—, —CH$_2$CH$_2$—COO—, —OCO—CH$_2$CH$_2$—, —CON(R)— or —N(R)CO—; R is hydrogen or methyl; Y is a terpenoid residue or a steroid residue; m is an integer from 0 to 20; and n is an integer from 0 to 3.

2. The compound according to claim 1, wherein the terpenoid residue is a residue of menthol, neomenthol, isomenthol, carveol, dihydrocarveol, terpinen-4-ol, verbenol, nopol, perillyl alcohol, cedrol, citronellol, dihydrocitronellol or isopinocampheol; and the steroid residue is a residue of sterol.

3. The compound according to claim 1, wherein in the formula (1), Y is a menthol residue or a cholesterol residue.

4. The compound according to claim 1, wherein in the formula (1), $-(A^1-Z^1)_n-A^2-$ is a divalent group represented by the following formula (2-1) or (2-2)

(2-1)

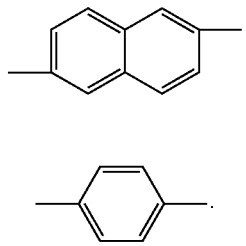

(2-2)

5. The compound according to claim 1, wherein in the formula (1), $-(A^1-Z^1)_n-A^2-$ is a divalent group represented by any one of the following formulas (3-1) to (3-7)

(3-1)

(3-2)

(3-3)

(3-4)

(3-5)

(3-6)

(3-7)

6. The compound according to claim 1, wherein in the formula (1), $-(A^1-Z^1)_n-A^2-$ is a divalent group represented by any one of the following formulas (4-1) to (4-8)

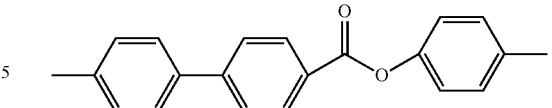 (4-1)

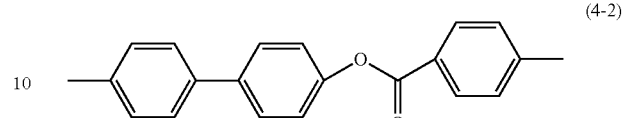 (4-2)

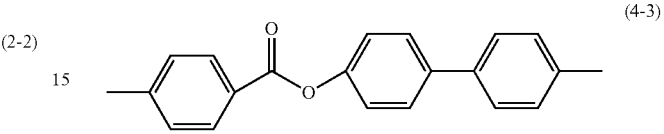 (4-3)

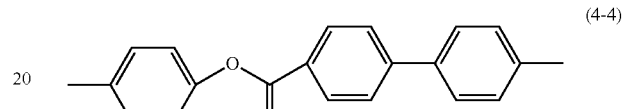 (4-4)

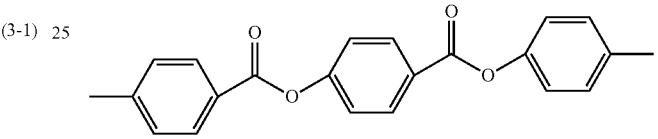 (4-5)

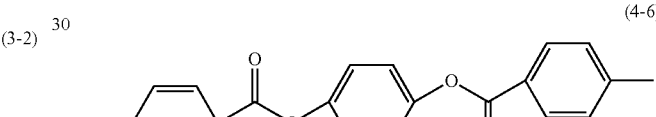 (4-6)

 (4-7)

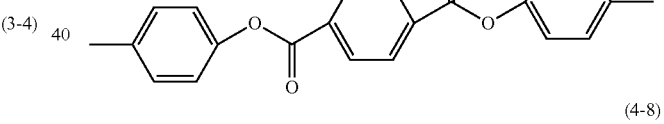 (4-8)

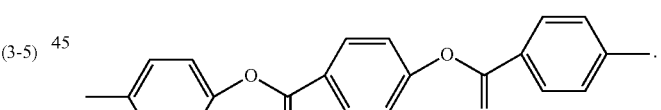

7. The compound according to claim 1, wherein in the formula (1), $-(A^1-Z^1)_n-A^2-$ is the following formula (3-1) and $X^1$ is —O—

(3-1)

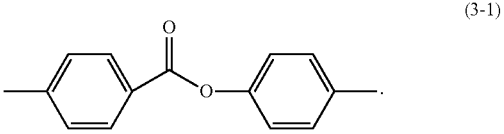

8. A liquid crystal composition, comprising the compound according to claim 1 and a liquid crystal compound.

9. The liquid crystal composition according to claim 8, wherein the composition comprises at least one polymerizable liquid crystal compound as the liquid crystal compound.

10. A polymer formed by polymerization of the liquid crystal composition according to claim 9.

11. The polymer according to claim 10, wherein the polymer exhibits a cholesteric phase.

* * * * *